US012633392B2

(12) United States Patent
Shelton, IV et al.

(10) Patent No.: US 12,633,392 B2
(45) Date of Patent: May 19, 2026

(54) MAPPING DATA PIPELINES FOR SURGICAL SYSTEMS

(71) Applicant: Cilag GmbH International, Zug (CH)

(72) Inventors: Frederick E. Shelton, IV, Hillsboro, OH (US); Jason L. Harris, Lebanon, OH (US); Matthew D. Cowperthwait, Cincinnati, OH (US); Shane R. Adams, Lebanon, OH (US); Nicholas James Ross, Franklin, OH (US)

(73) Assignee: Cilag GmbH International, Zug (CH)

( * ) Notice: Subject to any disclaimer, the term of this patent is extended or adjusted under 35 U.S.C. 154(b) by 10 days.

(21) Appl. No.: 18/960,047

(22) Filed: Nov. 26, 2024

(65) Prior Publication Data

US 2025/0174342 A1 May 29, 2025

Related U.S. Application Data

(60) Provisional application No. 63/603,031, filed on Nov. 27, 2023.

(51) Int. Cl.
G16H 20/40 (2018.01)
G16H 10/00 (2018.01)
(Continued)

(52) U.S. Cl.
CPC ............. G16H 20/40 (2018.01); G16H 10/00 (2018.01); G16H 10/60 (2018.01); G16H 40/40 (2018.01);
(Continued)

(58) Field of Classification Search
CPC ........ G16H 20/40; G16H 40/67; G16H 10/60; G16H 50/20; G16H 40/40; G16H 40/63;
(Continued)

(56) References Cited

U.S. PATENT DOCUMENTS 7,143,925 B2 12/2006 Shelton, IV et al.
8,317,070 B2 11/2012 Hueil et al.
(Continued)

FOREIGN PATENT DOCUMENTS

WO 2014151621 A1 9/2014

OTHER PUBLICATIONS

"Apache Hadoop", Wikipedia, Oct. 26, 2023. Retrieved from Wikipedia: https://en.wikipedia.org/w/index.php?title=Apache_Hadoop&oldid=1181994713, 8 pages.
(Continued)

*Primary Examiner* — Fonya M Long
*Assistant Examiner* — Anthony Balaj
(74) *Attorney, Agent, or Firm* — Condo Roccia Koptiw LLP

(57) ABSTRACT

Surgical systems and related computer-implemented methods are provided, including during performance of a surgical procedure on a patient, receiving, at a first surgical system, a first dataflow from a second surgical system, the first dataflow including first data regarding a measured patient parameter that the first surgical system is configured to use in performing a function during the performance of the surgical procedure. The computer-implemented methods including determining that a trigger event occurred during the performance of the surgical procedure such that a sum of a first bandwidth of the first dataflow and a second bandwidth of a second dataflow exceeds an available bandwidth, and in response to determining that the trigger event occurred, and during the performance of the surgical procedure, adjusting at least one of the first and second dataflows such that the sum of the first and second bandwidths does not exceed the available bandwidth.

17 Claims, 8 Drawing Sheets

(51) Int. Cl.

| | |
|---|---|
| *G16H 10/60* | (2018.01) |
| *G16H 40/40* | (2018.01) |
| *G16H 40/60* | (2018.01) |
| *G16H 40/63* | (2018.01) |
| *G16H 40/67* | (2018.01) |
| *G16H 50/20* | (2018.01) |
| *H04L 45/24* | (2022.01) |
| *H04L 47/726* | (2022.01) |
| *H04L 47/74* | (2022.01) |
| *H04L 47/80* | (2022.01) |

(52) U.S. Cl.
CPC ............. *G16H 40/60* (2018.01); *G16H 40/63* (2018.01); *G16H 40/67* (2018.01); *G16H 50/20* (2018.01); *H04L 45/24* (2013.01); *H04L 47/726* (2013.01); *H04L 47/746* (2013.01); *H04L 47/806* (2013.01)

(58) Field of Classification Search
CPC ........ G16H 40/60; G16H 10/00; H04L 45/24; H04L 47/726
See application file for complete search history.

(56) References Cited

U.S. PATENT DOCUMENTS

| | | |
|---|---|---|
| 8,393,514 B2 | 3/2013 | Shelton, IV et al. |
| 8,831,782 B2 | 9/2014 | Itkowitz |
| 8,989,903 B2 | 3/2015 | Weir et al. |
| 9,072,535 B2 | 7/2015 | Shelton et al. |
| 9,072,536 B2 | 7/2015 | Shelton, IV et al. |
| 9,439,649 B2 | 9/2016 | Shelton et al. |
| 9,804,618 B2 | 10/2017 | Leimbach et al. |
| 9,839,487 B2 | 12/2017 | Dachs |
| 9,877,783 B2 | 1/2018 | Van Der Weide et al. |
| 9,913,642 B2 | 3/2018 | Leimbach et al. |
| 10,052,044 B2 | 8/2018 | Shelton et al. |
| 10,172,611 B2 | 1/2019 | Shelton, IV et al. |
| 10,314,649 B2 | 6/2019 | Bakos et al. |
| 10,413,373 B2 | 9/2019 | Yates et al. |
| 10,531,929 B2 | 1/2020 | Widenhouse et al. |
| 10,543,051 B2 | 1/2020 | Schena et al. |
| 10,709,516 B2 | 7/2020 | Prisco et al. |
| 10,751,117 B2 | 8/2020 | Witt et al. |
| 10,758,310 B2 | 9/2020 | Shelton et al. |
| 10,849,697 B2 | 12/2020 | Yates et al. |
| 11,076,926 B2 | 8/2021 | Ragosta et al. |
| 11,160,602 B2 | 11/2021 | Shelton et al. |
| 11,219,501 B2 | 1/2022 | Shelton et al. |
| 11,266,458 B2 | 3/2022 | Perron et al. |
| 11,278,281 B2 | 3/2022 | Shelton et al. |
| 11,284,963 B2 | 3/2022 | Shelton et al. |
| 11,304,699 B2 | 4/2022 | Shelton et al. |
| 11,559,307 B2 | 1/2023 | Shelton et al. |
| 11,607,239 B2 | 3/2023 | Swensgard et al. |
| 11,678,881 B2 | 6/2023 | Yates et al. |
| 11,723,642 B2 | 8/2023 | Shelton et al. |
| 11,744,667 B2 | 9/2023 | Shelton et al. |
| 11,759,283 B2 | 9/2023 | Shelton et al. |
| 11,776,144 B2 | 10/2023 | Shelton et al. |
| 11,832,996 B2 | 12/2023 | Shelton et al. |
| 11,857,152 B2 | 1/2024 | Shelton et al. |
| 11,896,442 B2 | 2/2024 | Eckert et al. |
| 11,937,769 B2 | 3/2024 | Shelton et al. |
| 12,002,571 B2 | 6/2024 | Shelton et al. |
| 12,053,223 B2 | 8/2024 | Shelton et al. |
| 2013/0256377 A1 | 10/2013 | Schmid et al. |
| 2015/0129634 A1 | 5/2015 | Shelton, IV et al. |
| 2015/0133995 A1 | 5/2015 | Shelton et al. |
| 2015/0133996 A1 | 5/2015 | Shelton, IV et al. |
| 2015/0134076 A1 | 5/2015 | Shelton et al. |
| 2015/0134077 A1 | 5/2015 | Shelton, IV et al. |
| 2018/0101584 A1* | 4/2018 | Pattnaik .................. G06F 16/86 |
| 2018/0144018 A1* | 5/2018 | Hagiwara ................ G06F 9/52 |
| 2018/0177556 A1 | 6/2018 | Noonan |
| 2019/0132387 A1* | 5/2019 | Singh ...................... H04L 67/12 |
| 2019/0200844 A1 | 7/2019 | Shelton, IV et al. |
| 2019/0200981 A1 | 7/2019 | Harris et al. |
| 2019/0201046 A1 | 7/2019 | Shelton, IV et al. |
| 2019/0201112 A1 | 7/2019 | Wiener et al. |
| 2019/0201114 A1 | 7/2019 | Shelton, IV et al. |
| 2019/0201115 A1 | 7/2019 | Shelton et al. |
| 2019/0201140 A1 | 7/2019 | Yates et al. |
| 2019/0206004 A1 | 7/2019 | Shelton et al. |
| 2019/0206555 A1 | 7/2019 | Morgan et al. |
| 2019/0206556 A1 | 7/2019 | Shelton et al. |
| 2019/0206564 A1 | 7/2019 | Shelton et al. |
| 2019/0206569 A1 | 7/2019 | Shelton et al. |
| 2019/0207857 A1 | 7/2019 | Shelton, IV et al. |
| 2020/0000530 A1 | 1/2020 | Defonzo et al. |
| 2020/0085516 A1 | 3/2020 | Defonzo et al. |
| 2020/0170720 A1 | 6/2020 | Ummalaneni |
| 2020/0188043 A1 | 6/2020 | Yu et al. |
| 2021/0196108 A1 | 7/2021 | Shelton, IV et al. |
| 2021/0196383 A1 | 7/2021 | Shelton, IV et al. |
| 2022/0104896 A1 | 4/2022 | Shelton et al. |
| 2022/0187163 A1 | 6/2022 | Nakano |
| 2022/0233119 A1 | 7/2022 | Shelton et al. |
| 2022/0239577 A1 | 7/2022 | Shelton, IV |
| 2022/0273309 A1 | 9/2022 | Burbank et al. |
| 2022/0374443 A1* | 11/2022 | Fan ................... G06F 16/24564 |
| 2023/0023083 A1 | 1/2023 | Shelton et al. |
| 2023/0025061 A1 | 1/2023 | Shelton et al. |
| 2023/0026634 A1 | 1/2023 | Shelton et al. |
| 2023/0077141 A1 | 3/2023 | Scheib et al. |
| 2023/0095002 A1 | 3/2023 | Shelton et al. |
| 2023/0096268 A1 | 3/2023 | Shelton, IV et al. |
| 2023/0097906 A1 | 3/2023 | Shelton et al. |
| 2023/0098538 A1 | 3/2023 | Shelton et al. |
| 2023/0100698 A1 | 3/2023 | Shelton et al. |
| 2023/0101750 A1 | 3/2023 | Shelton et al. |
| 2023/0102358 A1 | 3/2023 | Shelton et al. |
| 2023/0103005 A1 | 3/2023 | Shelton et al. |
| 2023/0116781 A1 | 4/2023 | Shelton et al. |
| 2023/0372030 A1 | 11/2023 | Shelton et al. |
| 2023/0386655 A1* | 11/2023 | Kouvaras ............... G16H 50/20 |
| 2024/0112768 A1 | 4/2024 | Shelton et al. |
| 2024/0220763 A1 | 7/2024 | Shelton et al. |
| 2024/0221937 A1 | 7/2024 | Shelton et al. |

OTHER PUBLICATIONS

"Data Catalog", IBM, Jun. 9, 2022. Retrieved from The Wayback Machine: https://web.archive.org/web/20220609191251/https://www.ibm.com/topics/data-catalog, 7 pages.
"ELT vs. ETL: What's the Difference?", IBM, Retrieved from: https://www.ibm.com/think/topics/elt-vs-etl, Dec. 14, 2021, 4 pages.
U.S. Appl. No. 18/809,890 entitled "Synchronized Motion of Independent Surgical Devices" filed Aug. 20, 2024, 58 pages.
U.S. Appl. No. 18/809,960 entitled "Inter-Connectivity of Data Flows Between Independent Smart Systems" filed Aug. 20, 2024, 90 pages.
U.S. Appl. No. 18/810,036 entitled "Adaptive Interaction Between Smart Healthcare Systems" filed Aug. 20, 2024, 53 pages.
U.S. Appl. No. 18/810,041 entitled "Inter-Connectivity of Data Flows Between Independent Smart Systems" filed Aug. 20, 2024, 90 pages.
U.S. Appl. No. 18/810,082 entitled "Control Redirection and Image Porting Between Surgical Systems" filed Aug. 20, 2024, 62 pages.
U.S. Appl. No. 18/810,119 entitled "Processing and Display of Tissue Tension" filed Aug. 20, 2024, 52 pages.
U.S. Appl. No. 18/810,133 entitled "Synchronization of the Operational Envelopes of Independent Surgical Devices" filed Aug. 20, 2024, 48 pages.
U.S. Appl. No. 18/810,170 entitled "Synchronized Motion of Independent Surgical Devices to Maintain Relational Field of Views" filed Aug. 20, 2024, 44 pages.
U.S. Appl. No. 18/810,175 entitled "Situational Control of Smart Surgical Devices" filed Aug. 20, 2024, 43 pages.

(56)　　　　　References Cited

OTHER PUBLICATIONS

U.S. Appl. No. 18/810,208 entitled "Alignment and Distortion Compensation of Reference Planes Used by Surgical Devices" filed Aug. 20, 2024, 48 pages.

U.S. Appl. No. 18/810,222 entitled "Method for Activation Mode Determination of an Energy Device" filed Aug. 20, 2024, 67 pages.

U.S. Appl. No. 18/810,230 entitled "Shared Set of Object Registrations for Surgical Devices Using Independent Reference Planes" filed Aug. 20, 2024, 52 pages.

U.S. Appl. No. 18/810,266 entitled "Coordinated Control of Therapeutic Treatment Effects" filed Aug. 20, 2024, 48 pages.

U.S. Appl. No. 18/810,274 entitled "Visual Data-Based Activation Mode Determination of an Energy Device" filed Aug. 20, 2024, 67 pages.

U.S. Appl. No. 18/810,283 entitled "Functional Restriction of a System Based on Information From Another Independent System" filed Aug. 20, 2024, 42 pages.

U.S. Appl. No. 18/810,323 entitled "Method for Multi-System Interaction" filed Aug. 20, 2024, 353 pages.

U.S. Appl. No. 18/810,346 entitled "Electrical Data-Based Activation Mode Determination of an Energy Device" filed Aug. 20, 2024, 67 pages.

U.S. Appl. No. 18/810,355 entitled "Mechanical Data-Based Activation Mode Determination of an Energy Device" filed Aug. 20, 2024, 67 pages.

U.S. Appl. No. 18/810,361 entitled "Multi-Sourced Data-Based Activation Mode Determination of an Energy Device" filed Aug. 20, 2024, 68 pages.

U.S. Appl. No. 18/810,407 entitled "Conflict Resolution for Activation Mode Determination of an Energy Device" filed Aug. 20, 2024, 68 pages.

U.S. Appl. No. 18/810,419 entitled "Controlling Patient Monitoring Devices" filed Aug. 20, 2024, 45 pages.

"What are Smart Data Pipelines? Tools, Techniques, and Key Concepts", Software AG, Jul. 20, 2024. Retrieved from The Wayback Machine: https://web.archive.org/web/20240720225523/https://www.softwareag.com/en_corporate/resources/data-integration/article/data-pipelines.html, 11 pages.

"What is a Data Warehouse?", IBM, Jul. 11, 2023. Retrieved from The Wayback Machine: https://web.archive.org/web/20230711191853/https://www.ibm.com/topics/data-warehouse, 7 pages.

Albers, et al., "Adaptive On-the-Fly Changes in Distributed Processing Pipelines", Frontiers in Big Data, vol. 4, Article 666174, DOI: 10.3389/fdata.2021.666174, Nov. 26, 2021, pp. 1-20.

Bonack, Bryan, "Geofences: What They Are, What They Aren't, and Why They're Effective", Geospatial world, Retrieved from: https://geospatialworld.net/blogs/geofences-what-they-are-what-they-arent-and-why-theyre-effective/, Jul. 9, 2018, 3 pages.

Feldmann, Nate, "Data Lake or Data Swamp?", Nvisia, Retrieved from: https://www.nvisia.com/insights/data-swamp, Jul. 28, 2015, 7 pages.

Hunt, et al., "ZooKeeper: Wait-free Coordination for Internet-scale Systems", USENIX Annual Technical Conference, Retrieved from: https://www.usenix.org/conference/usenix-atc-10/zookeeper-wait-free-coordination-internet-scale-systems, 2010, pp. 1-14.

Kharat, et al., "Congestion Controlling Schemes for High-Speed Data Networks: A Survey", Journal of High Speed Networks, vol. 25, 2019, pp. 41-60.

Kirenz, Jan, "Introduction to Data Engineering", Retrieved from: https://kirenz.github.io/data-engineering/docs/intro.html, 2021, 4 pages.

Palmer, Matt, "Data Transformation: Types, Process, Benefits & Definition", ZUAR, Retrieved from https://www.zuar.com/blog/data-transformation-types-process-benefits-and-definition/, Oct. 1, 2022, 8 pages.

Wilson, et al., "Autonomic Thermoregulation", Oxford Research Encyclopedia of Neuroscience, Retrieved from https://www.semanticscholar.org/paper/Autonomic-Thermoregulation-Wilson-Metzler-Wilson/36346d04756860b32a715ec8e7ad9bff510f20e0, Aug. 28, 2018, 73 pages.

* cited by examiner

MAPPING DATA PIPELINES FOR SURGICAL SYSTEMS

CROSS REFERENCE TO RELATED APPLICATIONS

The present application claims priority to U.S. Provisional Patent Application No. 63/603,031 entitled "Smart Surgical Systems" filed Nov. 27, 2023, which is hereby incorporated by reference in its entirety.

The subject matter of the present application is related to the following patent applications filed on Nov. 26, 2024, which are hereby incorporated by reference in their entireties: U.S. application Ser. No. 18/960,006 entitled "Methods For Smart Surgical Systems," U.S. application Ser. No. 18/960,032 entitled "Data Flow Management Between Surgical Systems," U.S. application Ser. No. 18/960,059 entitled "Broadcast And Peer-To-Peer Communication For Surgical Systems," U.S. application Ser. No. 18/960,070 entitled "Data Lifecycle Management For Surgical Systems," U.S. application Ser. No. 18/960,081 entitled "Data Transformation For Surgical Systems," U.S. application Ser. No. 18/960,094 entitled "Geofencing For Surgical Systems," U.S. application Ser. No. 18/960,107 entitled "Information Discrimination For Surgical Instruments," and U.S. application Ser. No. 18/960,117 entitled "Adaptation Of Data Pipelines For Surgical Systems."

FIELD

The present disclosure relates generally to smart surgical devices, systems, and methods.

BACKGROUND

Surgical operations and environments have benefited from advances in technology. These advances include upgraded equipment, therapeutics, techniques, and more, which has resulted in more favorable outcomes for both patients and healthcare personnel. Further benefits can be realized through the continued advancement of technology and the continued integration of such advancements into the operations and environments.

Computers are more and ubiquitous in everyday life, and as the power of computers and computing systems increases, larger quantities of data can be processed in ways that render meaningful results and information for end users. This type of big data processing has immense benefits to surgical operations and environments as well, as more information can be distilled to meaningful assistance to a user, such as a surgeon, for use and reliance during surgical operations. Ultimately, this additional information for the user can result in even more favorable outcomes for both patients and healthcare personnel.

SUMMARY

In general, smart surgical devices, systems, and methods are provided.

In one embodiment, a surgical data management system is provided that includes a surgical hub. The surgical hub includes a processor and a memory storing instructions that, when executed by the processor, cause the processor to perform operations including: in response to a trigger event occurring during a performance of a surgical procedure on a patient, and in real time with the performance of the surgical procedure on the patient, dynamically change a mapping of a data pipeline communicatively coupling a plurality of surgical systems in use in association with the surgical procedure. Each of the plurality of surgical systems is configured to communicate data using the data pipeline, the data collected in relation to and in real time with the performance of the surgical procedure and including at least one of patient data, surgical procedure data, and surgical instrument data. The dynamic changing includes at least one of: changing a destination of the data pipeline, changing a source of the data pipeline, adding an additional data pipeline to the data pipeline, changing a data flow rate of the data pipeline, changing where data transformation occurs along the data pipeline, using a parallel data pipeline instead of a serial pipeline, using a serial data pipeline instead of a parallel pipeline, changing a communication protocol of the data pipeline, and changing a data transmission frequency of the data pipeline.

The surgical data management system can have any number of variations. For example, the trigger event can be a monitored patient parameter varying outside a predetermined threshold, and the dynamic changing can include at least changing where the data transformation occurs along the data pipeline such that untransformed data instead of transformed data is transmitted to at least one of the plurality of surgical systems along the data pipeline.

For another example, the trigger event can be a monitored patient parameter varying outside a predetermined threshold, and the dynamic changing can include at least changing the destination of the data pipeline so the destinations of the data pipeline includes a one of the plurality of surgical systems monitoring the patient parameter. Further, the instructions, when executed by the processor, can further cause the processor to perform operations including: after the dynamic changing, and in response to the monitored patient parameter no longer being outside the predetermined threshold, dynamically changing the mapping again so the so the destination of the data pipeline no longer all includes the one of the plurality of surgical systems monitoring the patient parameter.

For yet another example, the trigger event can be a predetermined aspect of the surgical procedure being performed, and the dynamic changing can include at least changing where the data transformation occurs along the data pipeline such that untransformed data instead of transformed data is transmitted to at least one of the plurality of surgical systems along the data pipeline.

For another example, the trigger event can be an additional surgical system connecting to the plurality of data pipelines, and the dynamic changing can include at least changing a destination of the data pipeline and changing a source of the data pipeline.

For yet another example, the trigger event can be a change in power status of at least one the plurality of surgical systems, and the dynamic changing can include at least one of changing a destination of at least one of the plurality of data pipelines, changing the a source of the data pipeline, and changing where the data transformation occurs along the data pipeline.

For still another example, the trigger event can be a change in system status of at least one the plurality of surgical systems, and the dynamic changing can include at least changing a destination of the data pipeline.

For another example, the trigger event can be a change in thermal status of at least one the plurality of surgical systems.

For yet another example, the trigger event can be a change in data integrity level of data communicated along at least one the plurality of surgical systems.

For still another example, the dynamic changing can include determining a magnitude of change needed for the mapping to reflect a changing need of the data communicated using the data pipeline.

For another example, the instructions, when executed by the processor, can further cause the processor to perform operations including: when the dynamic changing includes adding an additional data pipeline to the data pipeline, managing transmission of data on the additional data pipeline to maintain continuity of data.

For still another example, each of the plurality of surgical systems can be one of a hospital network, a database, a surgical instrument, or a surgical cart, e.g., both being surgical instruments, one being a surgical instrument and the other being a database, etc.

In another embodiment, a surgical data management system is provided that includes a cloud-based server. The cloud-based server includes a processor and a memory storing instructions that, when executed by the processor, cause the processor to perform operations including: in response to a trigger event occurring during a performance of a surgical procedure on a patient, and in real time with the performance of the surgical procedure on the patient, dynamically change a mapping of a data pipeline communicatively coupling a plurality of surgical systems in use in association with the surgical procedure. Each of the plurality of surgical systems is configured to communicate data using the data pipeline, the data collected in relation to and in real time with the performance of the surgical procedure and including at least one of patient data, surgical procedure data, and surgical instrument data. The dynamic changing includes at least one of: changing a destination of the data pipeline, changing a source of the data pipeline, adding an additional data pipeline to the data pipeline, changing a data flow rate of the data pipeline, changing where data transformation occurs along the data pipeline, using a parallel data pipeline instead of a serial pipeline, using a serial data pipeline instead of a parallel pipeline, changing a communication protocol of the data pipeline, and changing a data transmission frequency of the data pipeline.

The surgical data management system can have any number of variations. For example, the trigger event can be a monitored patient parameter varying outside a predetermined threshold, and the dynamic changing can include at least changing where the data transformation occurs along the data pipeline such that untransformed data instead of transformed data is transmitted to at least one of the plurality of surgical systems along the data pipeline.

For another example, the trigger event can be a monitored patient parameter varying outside a predetermined threshold, and the dynamic changing can include at least changing the destination of the data pipeline so the destinations of the data pipeline includes a one of the plurality of surgical systems monitoring the patient parameter. Further, the instructions, when executed by the processor, can further cause the processor to perform operations including: after the dynamic changing, and in response to the monitored patient parameter no longer being outside the predetermined threshold, dynamically changing the mapping again so the so the destination of the data pipeline no longer all includes the one of the plurality of surgical systems monitoring the patient parameter.

For yet another example, the trigger event can be a predetermined aspect of the surgical procedure being performed, and the dynamic changing can include at least changing where the data transformation occurs along the data pipeline such that untransformed data instead of transformed data is transmitted to at least one of the plurality of surgical systems along the data pipeline.

For another example, the trigger event can be an additional surgical system connecting to the plurality of data pipelines, and the dynamic changing can include at least changing a destination of the data pipeline and changing a source of the data pipeline.

For yet another example, the trigger event can be a change in power status of at least one the plurality of surgical systems, and the dynamic changing can include at least one of changing a destination of at least one of the plurality of data pipelines, changing the a source of the data pipeline, and changing where the data transformation occurs along the data pipeline.

For still another example, the trigger event can be a change in system status of at least one the plurality of surgical systems, and the dynamic changing can include at least changing a destination of the data pipeline.

For another example, the trigger event can be a change in thermal status of at least one the plurality of surgical systems.

For yet another example, the trigger event can be a change in data integrity level of data communicated along at least one the plurality of surgical systems.

For still another example, the dynamic changing can include determining a magnitude of change needed for the mapping to reflect a changing need of the data communicated using the data pipeline.

For another example, the instructions, when executed by the processor, can further cause the processor to perform operations including: when the dynamic changing includes adding an additional data pipeline to the data pipeline, managing transmission of data on the additional data pipeline to maintain continuity of data.

For still another example, each of the plurality of surgical systems can be one of a hospital network, a database, a surgical instrument, or a surgical cart, e.g., both being surgical instruments, one being a surgical instrument and the other being a database, etc.

In another embodiment, a computer-implemented method is provided that includes, in response to a trigger event occurring during a performance of a surgical procedure on a patient, and in real time with the performance of the surgical procedure on the patient, dynamically change a mapping of a data pipeline communicatively coupling a plurality of surgical systems in use in association with the surgical procedure. Each of the plurality of surgical systems is configured to communicate data using the data pipeline, the data collected in relation to and in real time with the performance of the surgical procedure and including at least one of patient data, surgical procedure data, and surgical instrument data, and the dynamic changing includes at least one of: changing a destination of the data pipeline, changing a source of the data pipeline, adding an additional data pipeline to the data pipeline, changing a data flow rate of the data pipeline, changing where data transformation occurs along the data pipeline, using a parallel data pipeline instead of a serial pipeline, using a serial data pipeline instead of a parallel pipeline, changing a communication protocol of the data pipeline, and changing a data transmission frequency of the data pipeline.

The method can have any number of variations. For example, the trigger event can be a monitored patient parameter varying outside a predetermined threshold, and the dynamic changing can include at least changing where the data transformation occurs along the data pipeline such that untransformed data instead of transformed data is transmitted to at least one of the plurality of surgical systems along the data pipeline.

For another example, the trigger event can be a monitored patient parameter varying outside a predetermined threshold, and the dynamic changing can include at least changing the destination of the data pipeline so the destinations of the data pipeline includes a one of the plurality of surgical systems monitoring the patient parameter. Further, the method can also include, after the dynamic changing, and in response to the monitored patient parameter no longer being outside the predetermined threshold, dynamically changing the mapping again so the so the destination of the data pipeline no longer all includes the one of the plurality of surgical systems monitoring the patient parameter.

For yet another example, the trigger event can be a predetermined aspect of the surgical procedure being performed, and the dynamic changing can include at least changing where the data transformation occurs along the data pipeline such that untransformed data instead of transformed data is transmitted to at least one of the plurality of surgical systems along the data pipeline.

For another example, the trigger event can be an additional surgical system connecting to the plurality of data pipelines, and the dynamic changing can include at least changing a destination of the data pipeline and changing a source of the data pipeline.

For yet another example, the trigger event can be a change in power status of at least one the plurality of surgical systems, and the dynamic changing can include at least one of changing a destination of at least one of the plurality of data pipelines, changing the a source of the data pipeline, and changing where the data transformation occurs along the data pipeline.

For still another example, the trigger event can be a change in system status of at least one the plurality of surgical systems, and the dynamic changing can include at least changing a destination of the data pipeline.

For another example, the trigger event can be a change in thermal status of at least one the plurality of surgical systems.

For yet another example, the trigger event can be a change in data integrity level of data communicated along at least one the plurality of surgical systems.

For still another example, the dynamic changing can include determining a magnitude of change needed for the mapping to reflect a changing need of the data communicated using the data pipeline.

For another example, the method can also include, when the dynamic changing includes adding an additional data pipeline to the data pipeline, managing transmission of data on the additional data pipeline to maintain continuity of data.

For still another example, each of the plurality of surgical systems can be one of a hospital network, a database, a surgical instrument, or a surgical cart, e.g., both being surgical instruments, one being a surgical instrument and the other being a database, etc.

BRIEF DESCRIPTION OF DRAWINGS

The present invention is described by way of reference to the accompanying figures which are as follows.

Figure 1:
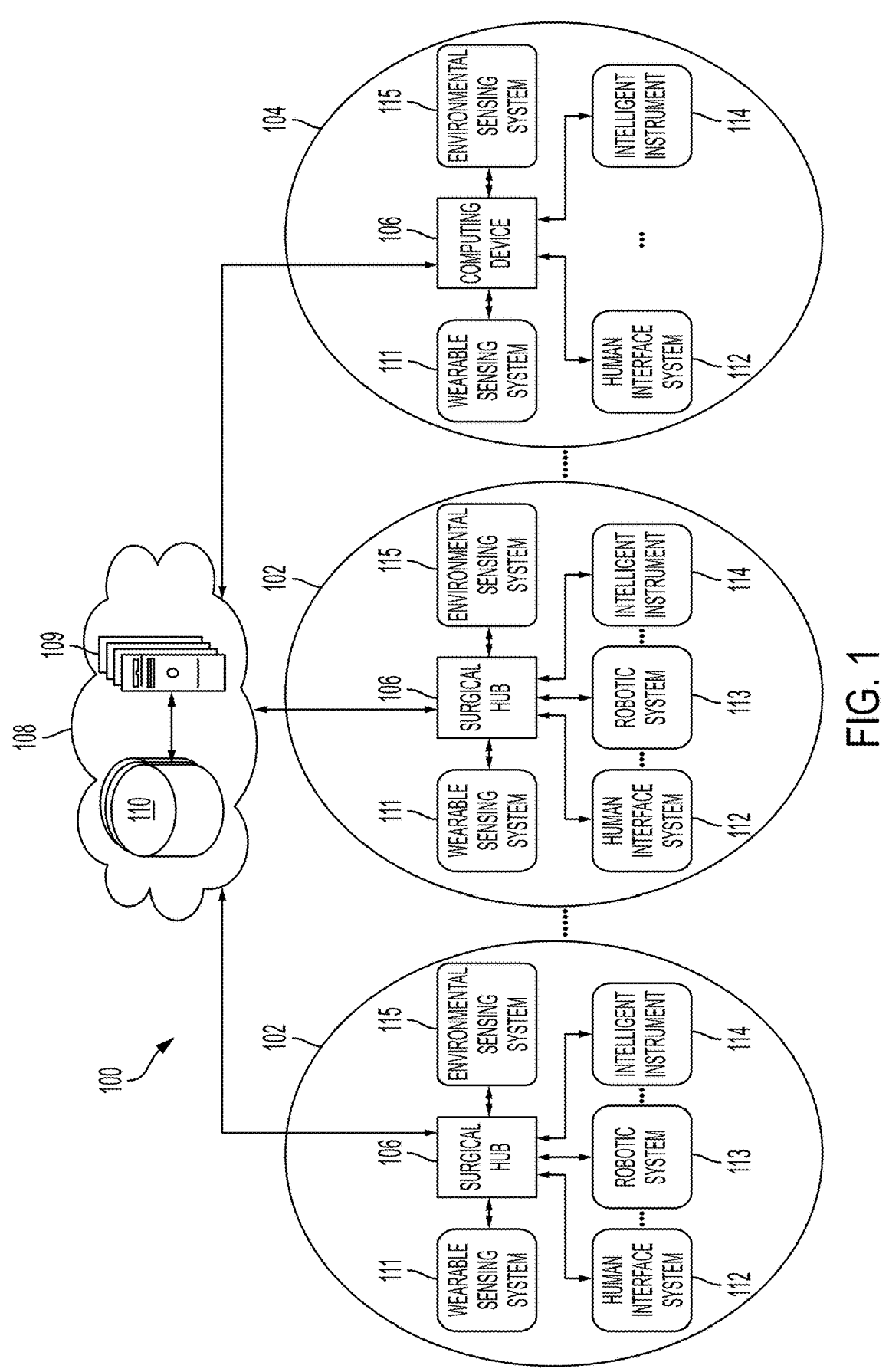
FIG. 1 is a schematic view of one embodiment of a computer-implemented surgical system.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

In general, a health data management system may include an interactive smart system that includes data origination facets, movement, architecture and management, and transformation and lifecycle to determine mechanisms by which smart systems talk to each other. The health data management system may include a data stack that defines handling of data from beginning to end. A data stack may include data sources, data pipelines, data transformation/modeling systems, and data storage systems that define end-to-end handling of data. In one embodiment, the health data management system may include a plurality of smart medical systems that are configured to perform one or more medical operations. The health data management system may utilize the data stack to control and manage data flow to the different smart device systems. In one embodiment, the health data management system may control and manage the data flow for managing a patient or performing a medical procedure, for example, providing surgical assistance during performance of a surgical procedure by one or more smart medical systems (also referred to herein as "surgical systems").

Surgical Systems

FIG. 1 shows one embodiment of a computer-implemented surgical system 100. The surgical system 100 may include one or more surgical systems (e.g., surgical subsystems) 102, 103, 104. As in this illustrated embodiment, the surgical system 100 may include first, second, and third surgical systems 102, 103, 104, but may instead include another number, e.g., one, two, four, etc.

The first surgical system 102 is discussed herein as a general representative of the surgical systems 102, 103, 104. For example, the surgical system 102 may include a computer-implemented interactive surgical system. For example, the surgical system 102 may include a surgical hub 106 and/or a computing device 116 in communication with a cloud computing system 108, for example, as described in FIG. 2.

The cloud computing system 108 may include at least one remote cloud server 109 and at least one remote cloud storage unit 110. Embodiments of surgical systems 102, 103, 104 may include one or more wearable sensing systems 111, one or more environmental sensing systems 115, one or more robotic systems (also referred to herein as "robotic surgical systems") 113, one or more intelligent instruments 114 (e.g., smart surgical instruments), one or more human interface systems 112, etc. A "human interface system" is also referred to herein as a "human interface device." The wearable sensing system(s) 111 may include one or more HCPs ("health care professional" or "health care personnel") sensing systems and/or one or more patient sensing systems. The environmental sensing system(s) 115 may include one or more devices used for measuring one or more environmental attributes, for example, as further described in FIG. 2. The robotic system(s) 113 may include a plurality of devices used for performing a surgical procedure, for example, as further described in FIG. 2.

Examples of robotic surgical systems include the Ottava™ robotic-assisted surgery system (Johnson & Johnson of New Brunswick, NJ), da Vinci® surgical systems (Intuitive Surgical, Inc. of Sunnyvale, CA), the Hugo™ robotic-assisted surgery system (Medtronic PLC of Minneapolis, MN), the Versius® surgical robotic system (CMR Surgical Ltd of Cambridge, UK), and the Monarch® platform (Auris Health, Inc. of Redwood City, CA). Embodiments of various robotic surgical systems and using robotic surgical systems are further described in, for example, U.S. Pat. App. Pub. No. 2018/0177556 entitled "Flexible Instrument Insertion Using An Adaptive Force Threshold" filed Dec. 28, 2016, U.S. Pat. App. Pub. No. 2020/0000530 entitled "Systems And Techniques For Providing Multiple Perspectives During Medical Procedures" filed Apr. 16, 2019, U.S. Pat. App. Pub. No. 2020/0170720 entitled "Image-Based Branch Detection And Mapping For Navigation" filed Feb. 7, 2020, U.S. Pat. App. Pub. No. 2020/0188043 entitled "Surgical Robotics System" filed Dec. 9, 2019, U.S. Pat. App. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical system 102 may be in communication with the one or more remote servers 109 that may be part of the cloud computing system 108. In an example embodiment, the surgical system 102 may be in communication with the one or more remote servers 109 via an internet service provider's cable/FIOS networking node. In an example embodiment, a patient sensing system may be in direct communication with the one or more remote servers 109. The surgical system 102 (and/or various sub-systems, smart surgical instruments, robots, sensing systems, and other computerized devices described herein) may collect data in real-time and transfer the data to the cloud computing system 108 for data processing and manipulation, e.g., by the one or more remote servers 109. It will be appreciated that cloud computing may rely on sharing computing resources rather than having local servers or personal devices to handle software applications.

The surgical system 102 and/or a component therein may communicate with the one or more remote servers 109 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G, and/or other wired or wireless communication protocols. Various embodiments of cloud-based analytics that may be performed by the cloud computing system 108 are described further in, for example, U.S. Pat. App Pub. No. 2019/0206569 entitled "Method Of Cloud Based Data Analytics For Use With The Hub" published Jul. 4, 2019, which is hereby incorporated by reference in its entirety.

The surgical hub 106 may have cooperative interactions with one or more means of displaying an image, e.g., a display configured to display an image from a laparoscopic scope, etc., and information from one or more other smart devices and/or one or more sensing systems. The surgical hub 106 may interact with the one or more sensing systems, the one or more smart devices, and the one or more means of displaying an image. The surgical hub 106 may be configured to gather measurement data from the sensing system(s) and send notifications or control messages to the sensing system(s). The surgical hub 106 may send and/or receive information including notification information to and/or from the one or more human interface systems 112. The one or more human interface systems 112 may include one or more human interface devices (HIDs). The surgical hub 106 may send and/or receive notification information or control information to audio, display and/or control information to various devices that are in communication with the surgical hub 106.

In an exemplary embodiment, the one or more sensing systems may include the one or more wearable sensing system 111 (which may include one or more HCP sensing systems and/or one or more patient sensing systems) and/or the environmental sensing system(s) 115 shown in FIG. 1. The sensing system(s) may measure data relating to various biomarkers.

In an exemplary embodiment, the sensing system(s) may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensor(s) may measure the biomarkers using one of more of the following sensing technologies: photoplethysmography, electrocardiography, electroencephalography, colorimetry, impedimentary, potentiometry, amperometry, etc.

The biomarkers measured by the sensing system(s) may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented surgical system 100, for example. The information from the biomarkers may be determined and/or used by the computer-implemented patient and the computer-implemented surgical system 100 to improve said systems and/or to improve patient outcomes, for example.

The sensing system(s) may send data to the surgical hub 106. The sensing system(s) may use one or more of the following radiofrequency (RF) protocols for communicating with the surgical hub 106: Bluetooth, Bluetooth Low-Energy (BLE), Bluetooth Smart, Zigbee, Z-wave, IPv6 Low-power wireless Personal Area Network (6LoWPAN), Wi-Fi, etc.

Various embodiments of sensing systems, biomarkers, and physiological systems are described further in, for example, U.S. Pat. App Pub. No. 2022/0233119 entitled "Method Of Adjusting A Surgical Parameter Based On Biomarker Measurements" filed published Jul. 28, 2022, which is hereby incorporated by reference in its entirety.

The sensing systems described herein may be employed to assess physiological conditions of a surgeon operating on a patient or a patient being prepared for a surgical procedure or a patient recovering after a surgical procedure. The cloud-based computing system 108 may be used to monitor biomarkers associated with a HCP (a surgeon, a nurse, etc.) or a patient in real-time and to generate surgical plans based at least on measurement data gathered prior to a surgical procedure, provide control signals to one or more surgical instruments during a surgical procedure, and notify a patient of a complication during a post-surgical period.

The cloud-based computing system 108 may be used to analyze surgical data. Surgical data may be obtained via the intelligent instrument(s) 114, the wearable sensing system(s) 111, the environmental sensing system(s) 115, the robotic system(s) 113, and/or the like in the surgical system 102. Surgical data may include tissue states to assess leaks or perfusion of sealed tissue after a tissue sealing and cutting procedure pathology data, including images of samples of body tissue, anatomical structures of the body using a variety of sensors integrated with imaging devices and techniques such as overlaying images captured by multiple imaging devices, image data, and/or the like. The surgical data may be analyzed to improve surgical procedure outcomes by determining if further treatment, such as the application of endoscopic intervention, emerging technologies, a targeted radiation, targeted intervention, and precise robotics to tissue-specific sites and conditions. Such data analysis may employ outcome analytics processing and using standardized approaches may provide beneficial feedback to either confirm surgical treatments and the behavior of the surgeon or suggest modifications to surgical treatments and the behavior of the surgeon.

Figure 2:
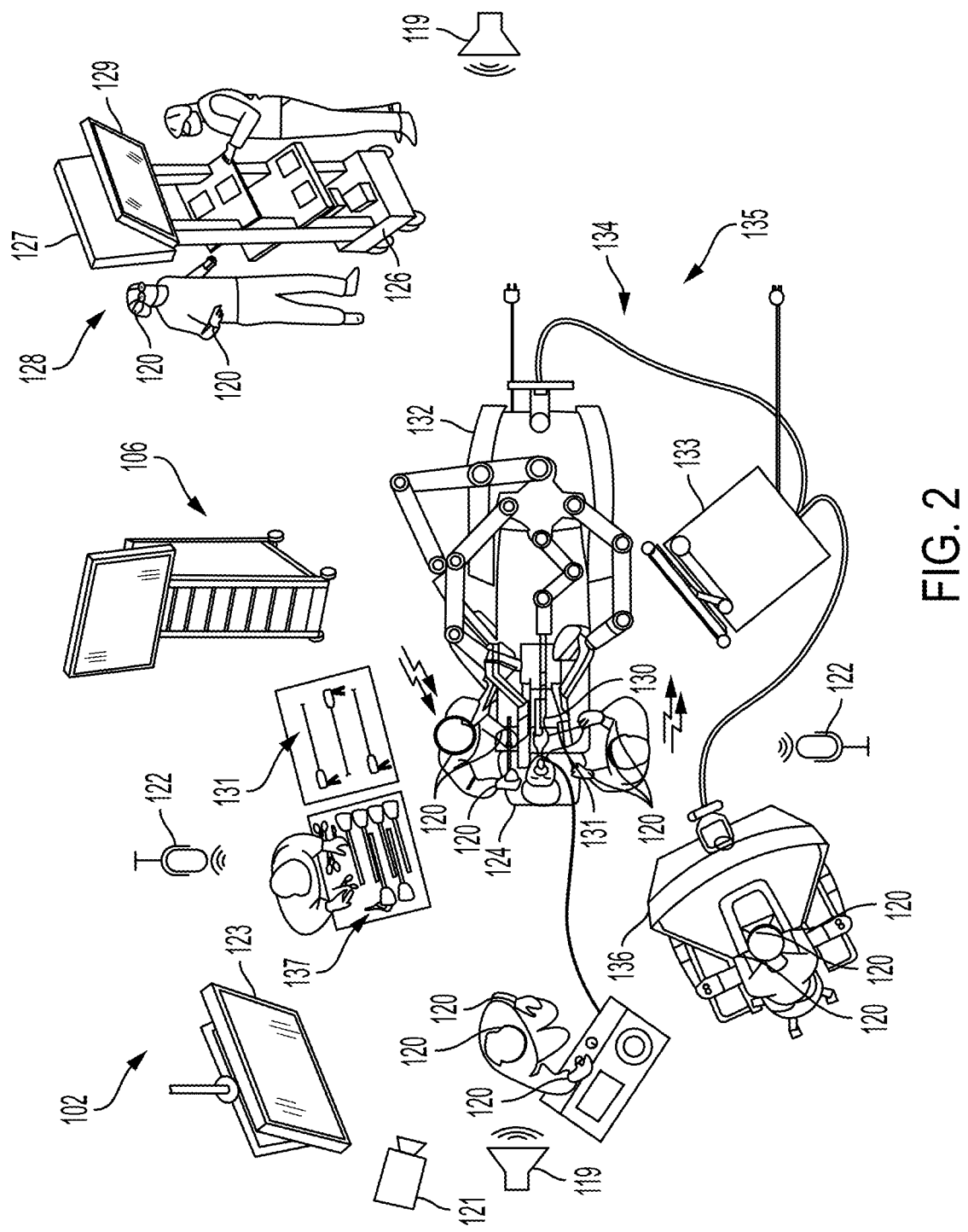
FIG. 2 is a perspective view of one embodiment of a surgical system in one embodiment of a surgical operating room.

FIG. 2 shows one embodiment of the surgical system 102 in one embodiment of a surgical operating room 135. As illustrated in FIG. 2, a patient is being operated on by one or more HCPs. The HCP(s) are being monitored by one or more HCP sensing systems 120 worn by the HCP(s). The HCP(s) and the environment surrounding the HCP(s) may also be monitored by one or more environmental sensing systems including, for example, one or more cameras 121, one or more microphones 122, and other sensors that may be deployed in the operating room. The one or more HCP sensing systems 120 and the environmental sensing systems may be in communication with the surgical hub 106, which in turn may be in communication with the one or more cloud servers 109 of the cloud computing system 108, as shown in FIG. 1. The one or more environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 123 and one or more audio output devices (e.g., speakers 119) are positioned in a sterile field of the surgical system 102 to be visible to an operator at an operating table 124. In addition, a visualization/notification tower 126 is positioned outside the sterile field. The visualization/notification tower 126 may include a first non-sterile human interactive device (HID) 127 and a second non-sterile HID 129, which may be displays and may face away from each other. The display 123 and the HIDs 127, 129 may include a touch screen allowing a human to interface directly with the HID 127, 129. A human interface system, guided by the surgical hub 106, may be configured to utilize the display 123 and the HIDs 127, 129 to coordinate information flow to operators inside and outside the sterile field. In an exemplary embodiment, the surgical hub 106 may cause an HID (e.g., the primary display 123) to display a notification and/or information about the patient and/or a surgical procedure step. In an exemplary embodiment, the surgical hub 106 may prompt for and/or receive input from personnel in the sterile field or in the non-sterile area. In an exemplary embodiment, the surgical hub 106 may cause one or more non-sterile HIDs 127, 129 to display a snapshot of a surgical site, as recorded by an imaging device 130, while maintaining a live feed of the surgical site on one or more sterile HIDs, e.g., the primary HID 123. The snapshot on the non-sterile HID(s) 127, 129 can permit a non-sterile operator to perform a diagnostic step relevant to the surgical procedure, for example.

The surgical hub 106 may be configured to route a diagnostic input or feedback entered by a non-sterile operator at the visualization tower 126 to the primary display 123 within the sterile field, where it can be viewed by a sterile operator at the operating table. In an exemplary embodiment, the input can be in the form of a modification to the snapshot displayed on the non-sterile HID(s) 127, 129, which can be routed to the one or more sterile HIDs, e.g., the primary display 123, by the surgical hub 106.

Various embodiments of surgical hubs are further described in, for example, U.S. Pat. App. Pub. No. 2024/0221937 entitled "Method For Advanced Algorithm Support" published Jul. 4, 2024, U.S. Pat. App. Pub. No. 2024/0112768 entitled "Method For Health Data And Consent Management" published Apr. 4, 2024, U.S. Pat. App. Pub. No. 2024/0220763 entitled "Data Volume Determination For Surgical Machine Learning Applications" published Jul. 2, 2024, U.S. Pat. App. Pub. No. 2019/0206564 entitled "Method For Facility Data Collection And Interpretation" published Jul. 4, 2019, U.S. Pat. App. Pub. No. 2023/0026634 entitled "Surgical Data System And Classification" published Jan. 26, 2023, U.S. Pat. App. Pub. No. 2019/0201115 entitled "Aggregation And Reporting Of Surgical Hub Data" published Jul. 4, 2019, U.S. Pat. App. Pub. No. 2023/0372030 entitled "Automatic Compilation, Annotation, And Dissemination Of Surgical Data To Systems To Anticipate Related Automated Operations" published Nov. 23, 2023, U.S. Pat. App. Pub. No. 2022/0104896 entitled "Interactive Information Overlay On Multiple Surgical Displays" published Apr. 7, 2022, U.S. Pat. No. 11,304,699 entitled "Method For Adaptive Control Schemes For Surgical Network Control And Interaction" issued Apr. 19, 2022, U.S. Pat. No. 10,849,697 entitled "Cloud Interface For Coupled Surgical Devices" issued Dec. 1, 2020, U.S. Pat. App. Pub. No. 2022/0239577 entitled "Ad Hoc Synchronization Of Data From Multiple Link Coordinated Sensing Systems" published Jul. 28, 2022, U.S. Pat. App. Pub. No. 2023/0025061 entitled "Surgical Data System And Management" published Jan. 26, 2023, U.S. Pat. App. Pub. No. 2023/0023083 entitled "Method Of Surgical System Power Management, Communication, Processing, Storage And Display" published Jan. 26, 2023, U.S. Pat. App. Pub. No. 2019/0206556 entitled "Real-Time Analysis Of Comprehensive Cost Of All Instrumentation Used In Surgery Utilizing Data Fluidity To Track Instruments Through Stocking And In-House Processes" published Jul. 4, 2019, U.S. Pat. App. Pub. No. 2023/0096268 entitled "Methods for Controlling Cooperative Surgical Instruments" filed Oct. 5, 2021, U.S. Pat. App. Pub. No. 2019/0200844 entitled "Method Of Hub Communication, Processing, Storage And Display" filed Dec. 4, 2018, U.S. Pat. App. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. App. Pub. No. 2019/0201046 entitled "Method For Controlling Smart Energy Devices" filed Dec. 4, 2018, U.S. Pat. App. Pub. No. 2019/0201114 entitled "Adaptive Control Program Updates For Surgical Hubs" filed Mar. 29, 2018, U.S. Pat. App. Pub. No. 2019/0201140 entitled "Surgical Hub Situational Awareness" filed Mar. 29, 2018, U.S. Pat. App. Pub. No. 2019/0206004 entitled "Interactive Surgical Systems With Condition Handling Of Devices And Data Capabilities" filed Mar. 29, 2018, U.S. Pat. App. Pub. No. 2019/0206555 entitled "Cloud-based Medical Analytics For Customization And Recommendations To A User" filed Mar. 29, 2018, U.S. Pat. No. 11,678,881 entitled "Spatial Awareness Of Surgical Hubs In Operating Rooms" filed Mar. 29, 2018, and U.S. Pat. App. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

As in the illustrated embodiment of FIG. 2, one or more surgical instruments 131 may be being used in the surgical procedure as part of the surgical system 102. The surgical hub 106 may be configured to coordinate information flow to at least one display showing the surgical instrument(s) 131. A diagnostic input or feedback entered by a non-sterile operator at the visualization tower 126 can be routed by the surgical hub 106 to the at least one display, e.g., the primary display 123, within the sterile field, where it can be viewed by the operator of the surgical instrument(s) 131.

Various embodiments of coordinating information flow and display and various embodiments of surgical instruments are described further in, for example, U.S. Pat. No. 11,937,769 entitled "Method Of Hub Communication, Processing, Storage And Display" issued Mar. 26, 2024, which is hereby incorporated by reference in its entirety.

Examples of surgical instruments include a surgical dissector, a surgical stapler, a surgical grasper, a surgical scope (e.g., an endoscope, a laparoscope, etc.), a surgical energy device (e.g., a mono-polar probe, a bi-polar probe, an ablation probe, an ultrasound device, an ultrasonic end effector, etc.), a surgical clip applier, etc.

Various embodiments of surgical instruments are described further in, for example, U.S. Pat. No. 11,723,642 entitled "Cooperative Access Hybrid Procedures" issued Aug. 14, 2023, U.S. Pat. App. Pub. No. 2013/0256377 entitled "Layer Comprising Deployable Attachment Members" filed Feb. 8, 2013, U.S. Pat. No. 8,393,514 entitled "Selectively Orientable Implantable Fastener Cartridge" filed Sep. 30, 2010, U.S. Pat. No. 8,317,070 entitled "Surgical Stapling Devices That Produce Formed Staples Having Different Lengths" filed Feb. 28, 2007, U.S. Pat. No. 7,143,925 entitled "Surgical Instrument Incorporating EAP Blocking Lockout Mechanism" filed Jun. 21, 2005, U.S. Pat. App. Pub. No. 2015/0134077 entitled "Sealing Materials for Use in Surgical Stapling" filed Nov. 8, 2013, U.S. Pat. App. Pub. No. 2015/0134076 entitled "Hybrid Adjunct Materials for Use in Surgical Stapling" filed Nov. 8, 2013, U.S. Pat. App. Pub. No. 2015/0133996 entitled "Positively Charged Implantable Materials and Method of Forming the Same" filed Nov. 8, 2013, U.S. Pat. App. Pub. No. 2015/0129634 entitled "Tissue Ingrowth Materials and Method of Using the Same" filed Nov. 8, 2013, U.S. Pat. App. Pub. No. 2015/0133995 entitled "Hybrid Adjunct Materials for Use in Surgical Stapling" filed Nov. 8, 2013, U.S. Pat. No. 9,913,642 entitled "Surgical Instrument Comprising a Sensor System" filed Mar. 26, 2014, U.S. Pat. No. 10,172,611 entitled "Adjunct Materials and Methods of Using Same in Surgical Methods for Tissue Sealing" filed Jun. 10, 2014, U.S. Pat. No. 8,989,903 entitled "Methods And Systems For Indicating A Clamping Prediction" filed Jan. 13, 2012, U.S. Pat. No. 9,072,535 entitled "Surgical Stapling Instruments With Rotatable Staple Deployment Arrangements" filed May 27, 2011, U.S. Pat. No. 9,072,536 entitled "Differential Locking Arrangements For Rotary Powered Surgical Instruments" filed Jun. 28, 2012, U.S. Pat. No. 10,531,929 entitled "Control Of Robotic Arm Motion Based On Sensed Load On Cutting Tool" filed Aug. 16, 2016, U.S. Pat. No. 10,709,516 entitled "Curved Cannula Surgical System Control" filed Apr. 2, 2018, U.S. Pat. No. 11,076,926 entitled "Manual Release For Medical Device Drive System" filed Mar. 21, 2018, U.S. Pat. No. 9,839,487 entitled "Method For Engaging Surgical Instrument With Teleoperated Actuator" filed Mar. 17, 2015, U.S. Pat. No. 10,543,051 entitled "Method For Engaging Surgical Instrument With Teleoperated Actuator" issued Jan. 28, 2020, U.S. Pat. No. 9,804,618 entitled "Systems And Methods For Controlling A Segmented Circuit" filed Mar. 25, 2014, U.S. Pat. No. 11,607,239 entitled "Systems And Methods For Controlling A Surgical Stapling And Cutting Instrument" filed Apr. 15, 2016, U.S. Pat. No. 10,052,044 entitled "Time Dependent Evaluation Of Sensor Data To Determine Stability, Creep, And Viscoelastic Elements Of Measures" filed Mar. 6, 2015, U.S. Pat. No. 9,439,649 entitled "Surgical Instrument Having Force Feedback Capabilities" filed Dec. 12, 2012, U.S. Pat. No. 10,751,117 entitled "Electrosurgical Instrument With Fluid Diverter" filed Sep. 23, 2016, U.S. Pat. No. 11,160,602 entitled "Control Of Surgical Field Irrigation" filed Aug. 29, 2017, U.S. Pat. No. 9,877,783 entitled "Energy Delivery Systems And Uses Thereof" filed Dec. 30, 2016, U.S. Pat. No. 11,266,458 entitled "Cryosurgical System With Pressure Regulation" filed Apr. 19, 2019, U.S. Pat. No. 10,314,649 entitled "Flexible Expandable Electrode And Method Of Intraluminal Delivery Of Pulsed Power" filed Aug. 2, 2012, U.S. Pat. App. Pub. No. 2023/0116781 entitled "Surgical Devices, Systems, And Methods Using Multi-Source Imaging" filed Oct. 5, 2021, U.S. Pat. App. Pub. No. 2023/0102358 entitled "Surgical Devices, Systems, And Methods Using Fiducial Identification And Tracking" filed Oct. 5, 2021, U.S. Pat. No. 10,413,373 entitled "Robotic Visualization And Collision Avoidance" filed Aug. 16, 2016, U.S. Pat. App. Pub. No. 2023/0077141 entitled "Robotically Controlled Uterine Manipulator" filed Sep. 21, 2021, and U.S. Pat. App. Pub. No. 2022/0273309 entitled "Stapler Reload Detection And Identification" filed May 16, 2022, which are hereby incorporated by reference herein in their entireties.

As shown in FIG. 2, the surgical system 102 can be used to perform a surgical procedure on the patient who is lying down on the operating table 124 in the surgical operating room 135. A robotic system 134 may be used in the surgical procedure as a part of the surgical system 102. The robotic system 134 may include a surgeon's console 136, a patient side cart 132 (surgical robot), and a surgical robotic hub 133. The patient side cart 132 can manipulate at least one removably coupled surgical instrument 137 through a minimally invasive incision in the body of the patient while the surgeon views the surgical site via the surgeon's console 136. An image of the surgical site can be obtained by the imaging device 130, which can be manipulated by the patient side cart 132 to orient the imaging device 130. The surgical robotic hub 133 can be used to process the images of the surgical site for subsequent display to the surgeon via the surgeon's console 136.

Various embodiments of robotic systems and various embodiments of surgical instruments are described further in, for example, U.S. Pat. No. 11,559,307 entitled "Method Of Robotic Hub Communication, Detection, And Control" issued Jan. 24, 2023, which is hereby incorporated by reference in its entirety.

The imaging device 130 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 130 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments. The illumination source(s) may be configured to radiate electromagnetic energy in the visible spectrum as well as the invisible spectrum. The visible spectrum, sometimes referred to as the "optical spectrum" or the "luminous spectrum," is the portion of the electromagnetic spectrum that is visible to (e.g., can be detected by) the human eye and may be referred to as "visible light" or simply "light." A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 130 is configured for use in a minimally invasive procedure. Examples of imaging devices include an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device 130 may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., infrared (IR) and ultraviolet (UV). Spectral imaging can allow extraction of additional information that the human eye fails to capture with its receptors for red, green, and blue. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," e.g., an operating or treatment room, necessitate the highest possible sterility of all medical devices and equipment. Part of that sterilization process is the need to sterilize anything that comes in contact with the patient or penetrates the sterile field, including the imaging device 130 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Various embodiments of multi-spectral imaging are described further in, for example, U.S. Pat. No. 11,937,769 entitled "Method Of Hub Communication, Processing, Storage And Display" filed Dec. 4, 2018, which is hereby incorporated by reference in its entirety.

The wearable sensing system(s) 111 illustrated in FIG. 1 may include the one or more HCP sensing systems 120 as shown in FIG. 2. The one or more HCP sensing systems 120 may include sensing system(s) to monitor and detect a set of physical states and/or a set of physiological states of an HCP. An HCP may be a surgeon or one or more healthcare personnel assisting the surgeon or other healthcare service providers in general. The HCP sensing system 120 may send the measurement data associated with a set of biomarkers and data associated with a physical state of the surgeon to the surgical hub 106 for further processing. In an exemplary embodiment, an HCP sensing system 120 may measure a set of biomarkers to monitor the heart rate of an HCP. In an exemplary embodiment, an HCP sensing system 120 worn on a surgeon's wrist (e.g., a watch or a wristband) may use an accelerometer to detect hand motion and/or shakes and determine the magnitude and frequency of tremors.

The environmental sensing system(s) 115 shown in FIG. 1 may send environmental information to the surgical hub 106. In an exemplary embodiment, the environmental sensing system(s) 115 may include a camera 121 for detecting hand/body position of an HCP. The environmental sensing system(s) 115 may include one or more microphones 122 for measuring ambient noise in the surgical theater. Other environmental sensing system(s) 115 may include one or more devices, for example, a thermometer to measure temperature, a hygrometer to measure humidity of the surroundings in the surgical theater, etc. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc. The surgical hub 106, alone or in communication with the cloud computing system 108, may use the surgeon biomarker measurement data and/or environmental sensing information to modify control algorithms of hand-held instruments or the averaging delay of a robotic interface, for example, to minimize tremors.

The surgical hub 106 may use the surgeon biomarker measurement data associated with an HCP to adaptively control the one or more surgical instruments 131. For example, the surgical hub 106 may send a control program to one of the one or more surgical instruments 131 to control the surgical instrument's actuators to limit or compensate for fatigue and use of fine motor skills. The surgical hub 106 may send the control program based on situational awareness and/or the context on importance or criticality of a task. The control program may instruct the instrument to alter operation to provide more control when control is needed.

Figure 3:
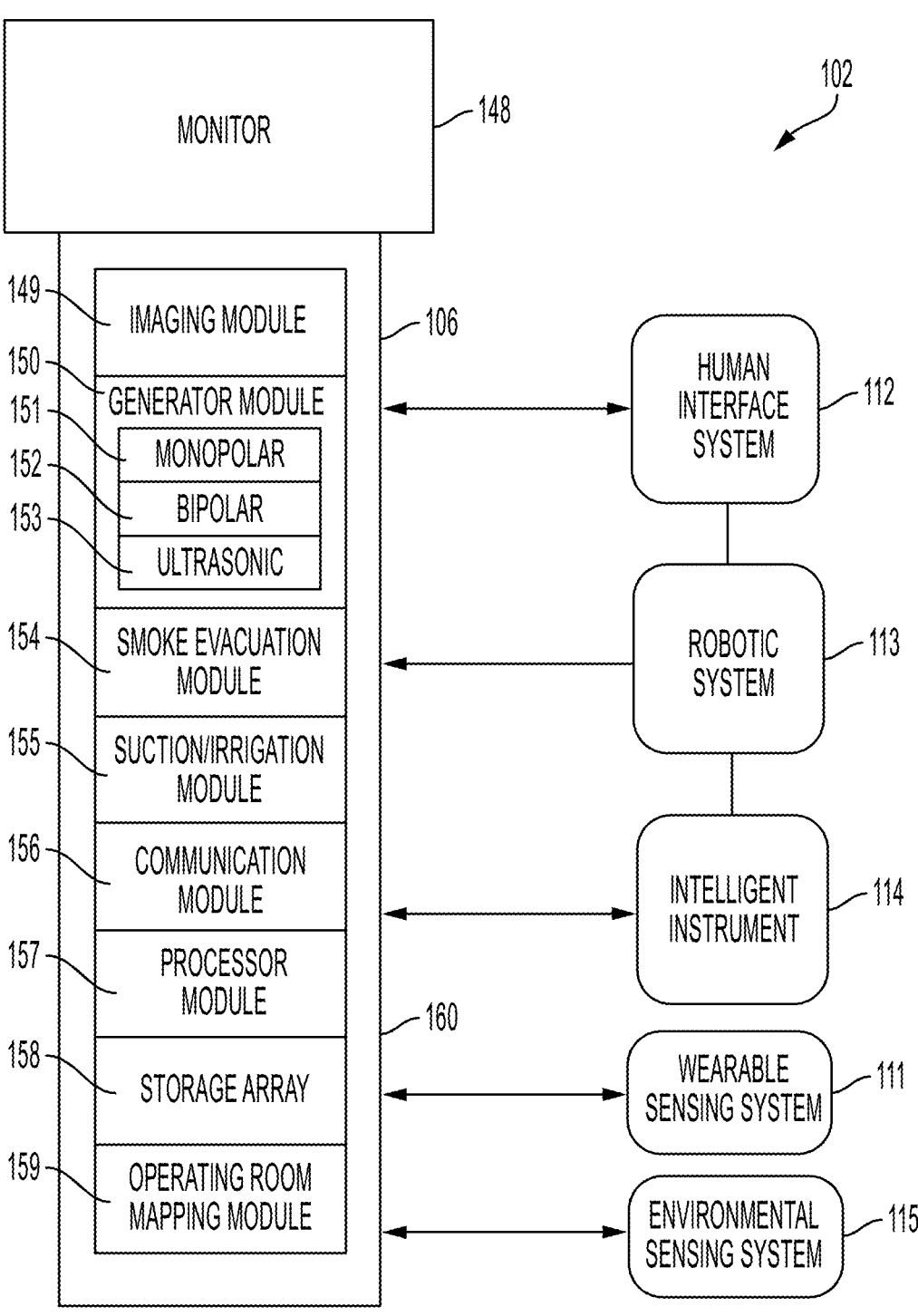
FIG. 3 is a schematic view of one embodiment of a surgical hub paired with various systems.

FIG. 3 shows an embodiment of the surgical system 102 including the surgical hub 106. The surgical hub 106 may be paired with, via a modular control, the one or more wearable sensing systems 111, the one or more environmental sensing systems 115, the one or more human interface systems 112, the one or more robotic systems 113, and the one or more intelligent instruments 114. As in this illustrated embodiment, the surgical hub 106 may include a display 148, an imaging module 149, a generator module 150 (e.g., an energy generator), a communication module 156, a processor module 157, a storage array 158, and an operating-room mapping module 159. In certain aspects, as illustrated in FIG. 3, the surgical hub 106 further includes a smoke evacuation module 154 and/or a suction/irrigation module 155. The various modules and systems may be connected to the modular control either directly via a router or via the communication module 156. The operating theater devices may be coupled to cloud computing resources and data storage, e.g., to the cloud computing system 108, via the modular control. The human interface system(s) 112 may include a display sub-system and a notification sub-system.

The modular control may be coupled to a non-contact sensor module. The non-contact sensor module may measure the dimensions of the operating theater and generate a map of the surgical theater using ultrasonic, laser-type, and/or the like non-contact measurement devices. Other distance sensors can be employed to determine the bounds of an operating room. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

An ultrasound-based non-contact sensor module may scan the operating theater by transmitting a burst of ultrasound and receiving the echo when it bounces off the perimeter walls of an operating theater as described further in, for example, U.S. Pat. No. 11,857,152 entitled "Surgical Hub Spatial Awareness To Determine Devices In Operating Theater" issued Jan. 2, 2024, U.S. Pat. No. 11,278,281 entitled "Interactive Surgical Platform" issued Mar. 22, 2022, and U.S. Prov. Pat. App. No. 62/611,341 entitled "Interactive Surgical Platform" filed Dec. 28, 2017, which are hereby incorporated by reference herein in their entireties.

During a surgical procedure, energy application to tissue, for sealing and/or cutting, may be associated with smoke evacuation, suction of excess fluid, and/or irrigation of the tissue. Fluid, power, and/or data lines from different sources may be entangled during the surgical procedure. Valuable time can be lost addressing this issue during a surgical procedure. Detangling the lines may necessitate disconnecting the lines from their respective modules, which may require resetting the modules. A hub modular enclosure 160 of the surgical hub 106 may offer a unified environment for managing the power, data, and fluid lines, which reduces the frequency of entanglement between such lines.

Energy may be applied to tissue at a surgical site. The surgical hub 106 may include the hub modular enclosure 160 and a combo generator module slidably receivable in a docking station of the hub modular enclosure 160. The docking station may include data and power contacts. The combo generator module may include two or more of: an ultrasonic energy generator component, a bipolar radiofrequency (RF) energy generator component, or a monopolar RF energy generator component that are housed in a single unit. The combo generator module may include a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. The fluid line may be a first fluid line, and a second fluid line may extend from the remote surgical site to a suction and irrigation module 155 slidably received in the hub modular enclosure 160. The hub modular enclosure 160 may include a fluid interface.

The combo generator module may generate multiple energy types for application to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. In an exemplary embodiment, the hub modular enclosure 160 may be configured to accommodate different generators and facilitate an interactive communication therebetween. The hub modular enclosure 160 may enable the quick removal and/or replacement of various modules.

The hub modular enclosure 160 may include a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. The modular surgical enclosure may include a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module.

As shown in FIG. 3, the hub modular enclosure 160 may allow the modular integration of the generator module 150, the smoke evacuation module 154, and the suction/irrigation module 155. The hub modular enclosure 160 may facilitate interactive communication between the operating-room mapping, smoke evacuation, and suction/irrigation modules 159, 154, 155. The generator module 150 can be with integrated monopolar, bipolar, and ultrasonic components supported in a single housing unit slidably insertable into the hub modular enclosure 160. The generator module 150 may connect to a monopolar device 151, a bipolar device 152, and an ultrasonic device 153. The generator module 150 may include a series of monopolar, bipolar, and/or ultrasonic generator modules that interact through the hub modular enclosure 160. The hub modular enclosure 160 may facilitate the insertion of multiple generators and interactive communication between the generators docked into the hub modular enclosure 160 so that the generators would act as a single generator.

A surgical data network having a set of communication hubs may connect the sensing system(s), the modular devices located in one or more operating theaters of a healthcare facility, a patient recovery room, or a room in a healthcare facility specially equipped for surgical operations, to the cloud computing system 108.

Figure 4:
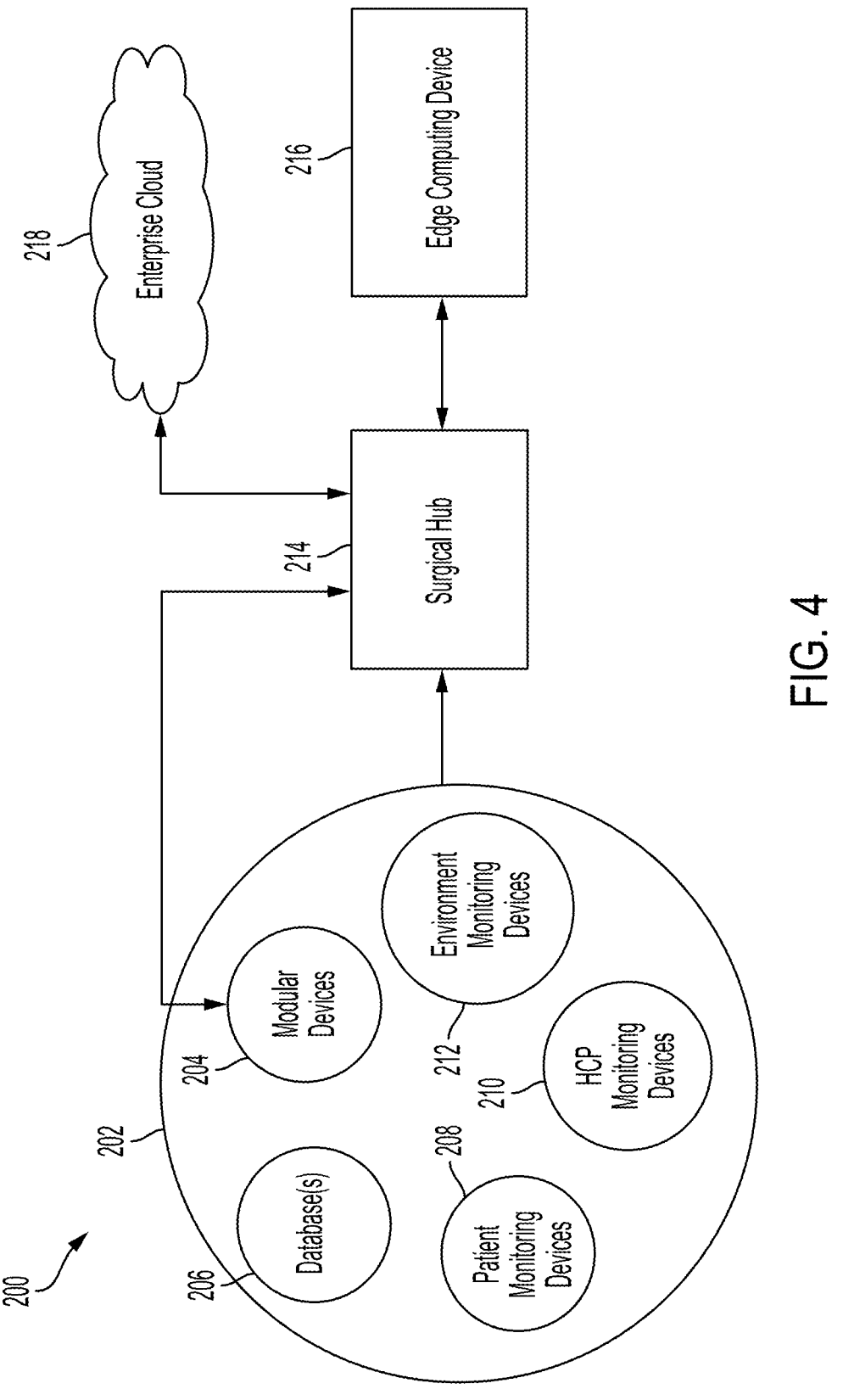
FIG. 4 is a schematic view of one embodiment of a situationally aware surgical system.

FIG. 4 illustrates one embodiment of a situationally aware surgical system 200. Data sources 202 of the situationally aware surgical system 200 may include, for example, modular devices 204, databases 206 (e.g., an electronic medical records (EMR) database, such as of a hospital or other medical facility, containing patient records, etc.), patient monitoring devices 208 (e.g., a blood pressure (BP) monitor, an electrocardiography (EKG) monitor, one or more wearable sensing systems 111, etc.), HCP monitoring devices 210 (e.g., one or more wearable sensing systems 111, etc.), and/or environment monitoring devices 212 (e.g., one or more environmental sensing systems 115, etc.).

The modular devices 204 may include sensors configured to detect parameters associated with a patient, HCPs and environment and/or the modular device 204 itself. The modular devices 204 may include the one or more intelligent instrument(s) 114.

The data sources 202 may be in communication (e.g., wirelessly or wired) with a surgical hub 214, such as the surgical hub 106. The surgical hub 214 may derive contextual information pertaining to a surgical procedure from data based upon, for example, the particular combination(s) of data received from the data sources 202 or the particular order in which the data is received from the data sources 202. The contextual information inferred from the received data can include, for example, the type of surgical procedure being performed, the particular step of the surgical procedure that a surgeon (and/or other HCP) is performing, the type of tissue being operated on, or a body cavity that is the subject of the surgical procedure. This ability by some aspects of the surgical hub 214 to derive or infer information related to the surgical procedure from received data can be referred to as "situational awareness." For example, the surgical hub 214 can incorporate a situational awareness system, which may be the hardware and/or programming associated with the surgical hub 214 that derives contextual information pertaining to the surgical procedure from the received data and/or a surgical plan information received from the edge computing system 216 or an enterprise cloud server 218, such as the cloud computing system 108. The contextual information derived from the data sources 202 may include, for example, what step of the surgical procedure is being performed, whether and how a particular modular device 204 is being used, and the patient's condition.

The surgical hub 214 may be connected to the databases 206 of the data sources 202 to retrieve therefrom data regarding the surgical procedure that is being performed or is to be performed. The data that may be received by the situational awareness system of the surgical hub 214 from the databases 206 may include, for example, start (or setup) time or operational information regarding the procedure (e.g., a segmentectomy in the upper right portion of the thoracic cavity). The surgical hub 214 may derive contextual information regarding the surgical procedure from this data alone or from the combination of this data and other data from the data sources 202.

The surgical hub 214 may be connected to (e.g., paired with) the patient monitoring devices 208 of the data sources 202. Examples of the patient monitoring devices 208 that can be paired with the surgical hub 214 may include a pulse oximeter (SpO$_2$ monitor), a blood pressure (BP) monitor, and an electrocardiogram (EKG) monitor. Perioperative data that is received by the situational awareness system of the surgical hub 214 from the patient monitoring devices 208 may include, for example, the patient's oxygen saturation, blood pressure, heart rate, and/or other physiological parameters. The contextual information that may be derived by the surgical hub 214 from the perioperative data transmitted by the patient monitoring devices 208 may include, for example, whether the patient is located in the operating theater or under anesthesia. The surgical hub 214 may derive these inferences from data from the patient monitoring devices 208 alone or in combination with data from other data from the data sources 202, such as a ventilator and/or other data source.

The surgical hub 214 may be connected to (e.g., paired with) the modular devices 204. Examples of the modular devices 204 that are paired with the surgical hub 214 may include a smoke evacuator, a medical imaging device such as the imaging device 130 shown in FIG. 2, an insufflator, a combined energy generator (for powering an ultrasonic surgical instrument and/or an RF electrosurgical instrument), and a ventilator.

The perioperative data received by the surgical hub 214 may be from a medical imaging device and/or other device(s). The perioperative data received by the surgical hub 214 from the medical imaging device may include, for example, whether the medical imaging device is activated and image data. The contextual information that is derived by the surgical hub 214 from the perioperative data sent by the medical imaging device may include, for example, whether the procedure is a video-assisted thoracic surgery (VATS) procedure (based on whether the medical imaging device is activated or paired to the surgical hub 214 at the beginning or during the course of the procedure). The image data (e.g., still image and/or video image) from the medical imaging device (or the data stream representing the video for a digital medical imaging device) may be processed by a pattern recognition system or a machine learning system to recognize features (e.g., organs or tissue types) in the field of view (FOV) of the medical imaging device, for example. The contextual information that is derived by the surgical hub 214 from the recognized features may include, for example, what type of surgical procedure (or step thereof) is being performed, what organ is being operated on, or what body cavity is being operated in.

The situational awareness system of the surgical hub 214 may derive the contextual information from the data received from the data sources 202 in a variety of different ways. For example, the situational awareness system can include a pattern recognition system, or a machine learning system (e.g., an artificial neural network), that has been trained on training data to correlate various inputs (e.g., data from the databases 206, the patient monitoring devices 208, the modular devices 204, the HCP monitoring devices 210, and/or the environment monitoring devices 212) to corresponding contextual information regarding a surgical procedure. For example, a machine learning system may accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling one or more of the modular devices 204. In examples, the contextual information received by the situational awareness system of the surgical hub 214 can be associated with a particular control adjustment or set of control adjustments for one or more of the modular devices 204. In examples, the situational awareness system can include a machine learning system, lookup table, or other such system, which may generate or retrieve one or more control adjustments for one or more of the modular devices 204 when provided the contextual information as input.

For example, based on data from the data sources 202, the surgical hub 214 may determine what type of tissue was being operated on. The surgical hub 214 can infer whether a surgical procedure being performed is a thoracic or an abdominal procedure, allowing the surgical hub 214 to determine whether the tissue clamped by an end effector of a surgical stapling and cutting instrument is lung tissue (for a thoracic procedure) or stomach tissue (for an abdominal procedure) tissue. The surgical hub 214 may determine whether the surgical site is under pressure (by determining that the surgical procedure is utilizing insufflation) and determine the procedure type, for a consistent amount of smoke evacuation for both thoracic and abdominal procedures. Based on data from the data sources 202, the surgical hub 214 may determine what step of the surgical procedure is being performed or will subsequently be performed.

The surgical hub 214 may determine what type of surgical procedure is being performed and customize an energy level according to an expected tissue profile for the surgical procedure. The situationally aware surgical hub 214 may adjust the energy level for an ultrasonic surgical instrument or RF electrosurgical instrument throughout the course of a surgical procedure, rather than just on a procedure-by-procedure basis.

In examples, data can be drawn from one or more data sources 202 to improve the conclusions that the surgical hub 214 draws from another one of the data sources 202. The surgical hub 214 may augment data that it receives from the modular devices 204 with contextual information that it has built up regarding the surgical procedure from the other data sources 202.

The situational awareness system of the surgical hub 214 can consider the physiological measurement data to provide additional context in analyzing the visualization data. The additional context can be useful when the visualization data may be inconclusive or incomplete on its own.

The surgical hub 214 may determine whether a surgeon (and/or other HCP(s)) was making an error or otherwise deviating from the expected course of action during the course of a surgical procedure. For example, the surgical hub 214 may determine a type of surgical procedure being performed, retrieve a corresponding list of steps or order of equipment usage (e.g., from a memory of the surgical hub 214 or other computer system), and compare the steps being performed or the equipment being used during the course of the surgical procedure to the expected steps or equipment for the type of surgical procedure that the surgical hub 214 determined is being performed. The surgical hub 214 can provide an alert indicating that an unexpected action is being performed or an unexpected device is being utilized at the particular step in the surgical procedure.

The surgical instruments (and other modular devices 204) may be adjusted for the particular context of each surgical procedure (such as adjusting to different tissue types) and validating actions during a surgical procedure. Next steps, data, and display adjustments may be provided to surgical instruments (and other modular devices 204) in the surgical theater according to the specific context of the surgical procedure.

Embodiments of situational awareness systems and using situational awareness systems during performance of a surgical procedure are described further in, for example, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729, 729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, which are hereby incorporated by reference in their entireties.

Figure 5:
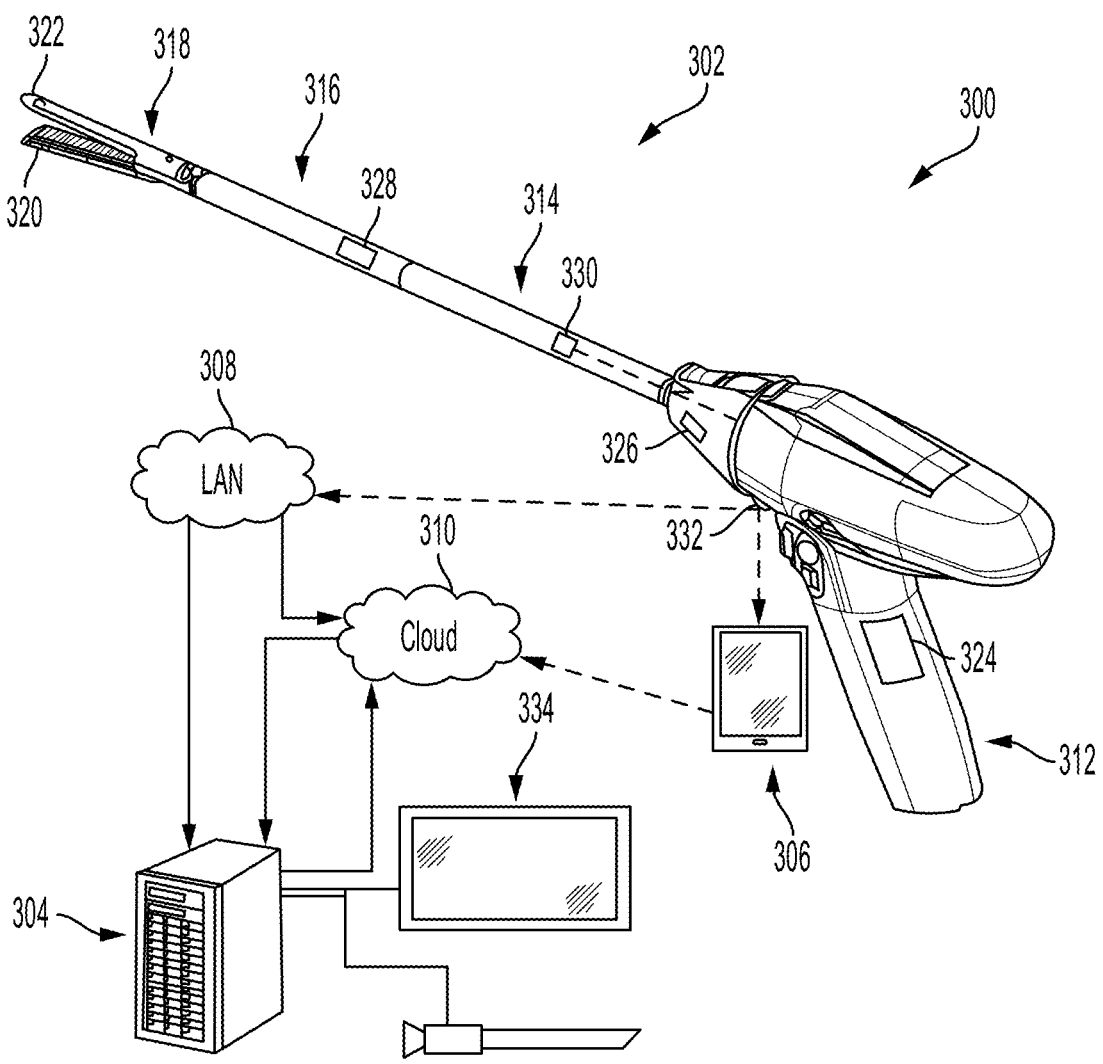
FIG. 5 is a perspective view of one embodiment of a surgical instrument and one embodiment of a surgical system that includes the surgical instrument.

FIG. 5 illustrates one embodiment of a surgical system 300 that may include a surgical instrument 302, such as the surgical instrument 114 of FIG. 1 or the surgical instrument 131 of FIG. 2. The surgical instrument 302 can be in communication with a console 304 and/or a portable device 306 through a local area network (LAN) 308 and/or a cloud network 310, such as the cloud computing system 108 of FIG. 1, via a wired and/or wireless connection. The console 304 and the portable device 306 may be any suitable computing device.

The surgical instrument 302 may include a handle 312, an adapter 314, and a loading unit 316. The adapter 314 releasably couples to the handle 312 and the loading unit 316 releasably couples to the adapter 314 such that the adapter 314 transmits a force from one or more drive shafts to the loading unit 316. The adapter 314 or the loading unit 316 may include a force gauge (not explicitly shown in FIG. 5) disposed therein to measure a force exerted on the loading unit 316. In some embodiments, the adapter 314 is non-releasably attached to the handle 312. In some embodiments, the adapter 314 and the loading unit 316 are integral and may be releasably attachable to the handle 312 or non-releasably attached to the handle 312.

The loading unit 316 may include an end effector 318 having a first jaw 320 and a second jaw 322. The loading unit 316 may be an in-situ loaded or multi-firing loading unit (MFLU) that allows a clinician to fire a plurality of fasteners (e.g., staples, clips, etc.) multiple times without requiring the loading unit 316 to be removed from a surgical site to reload the loading unit 316. The first and second jaws 320, 322 may be configured to clamp tissue therebetween, fire fasteners through the clamped tissue, and sever the clamped tissue. The first jaw 320 may be configured to fire at least one fastener a plurality of times or may be configured to include a replaceable multi-fire fastener cartridge including a plurality of fasteners that may be fired more than one time prior to being replaced. The second jaw 322 may include an anvil that deforms or otherwise secures the fasteners, as the fasteners are ejected from the multi-fire fastener cartridge.

The surgical instrument 302 may include a motor, such as at the handle 312, that is coupled to the one or more drive shafts to affect rotation of the one or more drive shafts. The surgical instrument 302 may include a control interface, such as at the handle 312, to selectively activate the motor. The control interface may include buttons, switches, levers, sliders, touchscreens, and/or any other suitable input mechanisms or user interfaces, which can be engaged by a clinician to activate the motor.

The control interface of the surgical instrument 302 may be in communication with a controller 324 (e.g., a microprocessor or other controller) of the surgical instrument 302, shown in the embodiment of FIG. 5 disposed in the handle 312, to selectively activate the motor to affect rotation of the one or more drive shafts. The controller 324 may be configured to receive input from the control interface, adapter data from the adapter 314, and loading unit data from the loading unit 316. The controller 324 may analyze the input from the control interface and the data received from the adapter 314 and/or the date received from the loading unit 316 to selectively activate the motor. The surgical instrument 302 may also include a display, such as at the handle 312, that is viewable by a clinician during use of the surgical instrument 302. The display may be configured to display portions of the adapter data and/or loading unit data before, during, or after firing of the surgical instrument 302.

The adapter 314 may include an adapter identification device 326 disposed therein, and the loading unit 316 may include a loading unit identification device 328 disposed therein. The adapter identification device 326 may be in communication with the controller 324, and the loading unit identification device 328 may be in communication with the controller 324. It will be appreciated that the loading unit identification device 328 may be in communication with the adapter identification device 326, which relays or passes communication from the loading unit identification device 328 to the controller 324. In embodiments in which the adapter 314 and the loading unit 316 are integral, one of the adapter identification device 326 and the loading unit identification device 328 may be omitted.

The adapter 314 may also include one or more sensors 330 disposed thereabout to detect various conditions of the adapter 314 or of the environment (e.g., if the adapter 314 is connected to a loading unit, if the adapter 314 is connected to a handle, if the one or more drive shafts are rotating, a torque of the one or more drive shafts, a strain of the one or more drive shafts, a temperature within the adapter 314, a number of firings of the adapter 314, a peak force of the adapter 314 during firing, a total amount of force applied to the adapter 314, a peak retraction force of the adapter 314, a number of pauses of the adapter 314 during firing, etc.). The one or more sensors 330 may provide an input to the adapter identification device 326 (or to the loading unit identification device 328 if the adapter identification device 326 is omitted) in the form of data signals. The data signals of the one or more sensors 330 may be stored within or be used to update the adapter data stored within the adapter identification device 326 (or the loading unit identification device 328 if the adapter identification device 326 is omitted). The data signals of the one or more sensors 330 may be analog or digital. The one or more sensors 330 may include, for example, a force gauge to measure a force exerted on the loading unit 316 during firing.

The handle 312 and the adapter 314 can be configured to interconnect the adapter identification device 326 and the loading unit identification device 328 with the controller 324 via an electrical interface. The electrical interface may be a direct electrical interface (e.g., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 326 and the controller 324 may be in wireless communication with one another via a wireless connection separate from the electrical interface.

The handle 312 may include a transceiver 332 that is configured to transmit instrument data from the controller 324 to one or more other components of the surgical system 300 (e.g., the LAN 308, the cloud 310, the console 304, and/or the portable device 306). The controller 324 may also transmit instrument data and/or measurement data associated with the one or more sensors 330 to a surgical hub, such as the surgical hub 106 of FIGS. 1-3 or the surgical hub 214 of FIG. 4. The transceiver 332 may receive data (e.g., cartridge data, loading unit data, adapter data, and/or other notifications) from the surgical hub. The transceiver 332 may receive data (e.g., cartridge data, loading unit data, or adapter data) from the other components of the surgical system 300. For example, the controller 324 may transmit surgical instrument data including a serial number of an attached adapter (e.g., the adapter 314) attached to the handle 312, a serial number of a loading unit (e.g., the loading unit 316) attached to the adapter 314, and a serial number of a multi-fire fastener cartridge loaded into the loading unit 316, e.g., into one of the jaws 320, 322 at the end effector 318, to the console 304. Thereafter, the console 304 may transmit data (e.g., cartridge data, loading unit data, and/or adapter data) associated with the attached cartridge, the loading unit 316, and the adapter, 314 respectively, back to the controller 324. The controller 324 can display messages on the local instrument display or transmit the message, via transceiver 332, to the console 304 or the portable device 306 to display the message on a display 334 or device screen of the portable device 306, respectively.

Various exemplary embodiments of aspects of smart surgical systems, for example how smart surgical systems choose to interact with each other, are described further in, for example, U.S. patent application Ser. No. 18/810,323 entitled "Method For Multi-System Interaction" filed Aug. 20, 2024, U.S. patent application Ser. No. 18/810,036 entitled "Adaptive Interaction Between Smart Healthcare Systems" filed Aug. 20, 2024, U.S. patent application Ser. No. 18/810,082 entitled "Control Redirection And Image Porting Between Surgical Systems" filed Aug. 20, 2024, U.S. patent application Ser. No. 18/809,890 entitled "Synchronized Motion Of Independent Surgical Devices" filed Aug. 20, 2024, U.S. patent application Ser. No. 18/810,133 entitled "Synchronization Of The Operational Envelopes Of Independent Surgical Devices" filed Aug. 20, 2024, U.S. patent application Ser. No. 18/810,170 entitled "Synchronized Motion Of Independent Surgical Devices To Maintain Relational Field Of Views" filed Aug. 20, 2024, U.S. patent application Ser. No. 18/810,208 entitled "Alignment And Distortion Compensation Of Reference Planes Used By Surgical Devices" filed Aug. 20, 2024, U.S. patent application Ser. No. 18/810,230 entitled "Shared Set Of Object Registrations For Surgical Devices Using Independent Reference Planes" filed Aug. 20, 2024, U.S. patent application Ser. No. 18/810,266 entitled "Coordinated Control Of Therapeutic Treatment Effects" filed Aug. 20, 2024, U.S. patent application Ser. No. 18/810,283 entitled "Functional Restriction Of A System Based On Information From Another Independent System" filed Aug. 20, 2024, U.S. patent application Ser. No. 18/809,960 entitled "Inter-Connectivity Of Data Flows Between Independent Smart Systems" filed Aug. 20, 2024, U.S. patent application Ser. No. 18/810,041 entitled "Inter-Connectivity Of Data Flows Between Independent Smart Systems" filed Aug. 20, 2024, U.S. patent application Ser. No. 18/810,119 entitled "Processing And Display Of Tissue Tension" filed Aug. 20, 2024, U.S. patent application Ser. No. 18/810,175 entitled "Situational Control Of Smart Surgical Devices" filed Aug. 20, 2024, U.S. patent application Ser. No. 18/810,222 entitled "Method For Activation Mode Determination Of An Energy Device" filed Aug. 20, 2024, U.S. patent application Ser. No. 18/810,274 entitled "Visual Data-Based Activation Mode Determination Of An Energy Device" filed Aug. 20, 2024, U.S. patent application Ser. No. 18/810,346 entitled "Electrical Data-Based Activation Mode Determination Of An Energy Device" filed Aug. 20, 2024, U.S. patent application Ser. No. 18/810,355 entitled "Mechanical Data-Based Activation Mode Determination Of An Energy Device" filed Aug. 20, 2024, U.S. patent application Ser. No. 18/810,361 entitled "Multi-Sourced Data-Based Activation Mode Determination Of An Energy Device" filed Aug. 20, 2024, U.S. patent application Ser. No. 18/810,407 entitled "Conflict Resolution For Activation Mode Determination Of An Energy Device" filed Aug. 20, 2024, and U.S. patent application Ser. No. 18/810,419 entitled "Controlling Patient Monitoring Devices" filed Aug. 20, 2024, which are each hereby incorporated by reference in their entireties.

Operating Intelligent Surgical Instruments

An intelligent surgical instrument, such as the surgical instrument 114 of FIG. 1, the surgical instrument 131 of FIG. 2, or the surgical instrument 302 of FIG. 5, can have an algorithm stored thereon, e.g., in a memory thereof, configured to be executable on board the intelligent surgical instrument, e.g., by a processor thereof, to control operation of the intelligent surgical instrument. In some embodiments, instead of or in addition to being stored on the intelligent surgical instrument, the algorithm can be stored on a surgical hub, e.g., in a memory thereof, that is configured to communicate with the intelligent surgical instrument.

The algorithm may be stored in the form of one or more sets of pluralities of data points defining and/or representing instructions, notifications, signals, etc. to control functions of the intelligent surgical instrument. In some embodiments, data gathered by the intelligent surgical instrument can be used by the intelligent surgical instrument, e.g., by a processor of the intelligent surgical instrument, to change at least one variable parameter of the algorithm. As discussed above, a surgical hub can be in communication with an intelligent surgical instrument, so data gathered by the intelligent surgical instrument can be communicated to the surgical hub and/or data gathered by another device in communication with the surgical hub can be communicated to the surgical hub, and data can be communicated from the surgical hub to the intelligent surgical instrument. Thus, instead of or in addition to the intelligent surgical instrument being configured to change a stored variable parameter, the surgical hub can be configured to communicate the changed at least one variable, alone or as part of the algorithm, to the intelligent surgical instrument and/or the surgical hub can communicate an instruction to the intelligent surgical instrument to change the at least one variable as determined by the surgical hub.

The at least one variable parameter may be among the algorithm's data points, e.g., may be included in instructions for operating the intelligent surgical instrument, and are thus each able to be changed by changing one or more of the stored pluralities of data points of the algorithm. After the at least one variable parameter has been changed, subsequent execution of the algorithm can be according to the changed algorithm. As such, operation of the intelligent surgical instrument over time can be managed for a patient to increase the beneficial results use of the intelligent surgical instrument by taking into consideration actual situations of the patient and actual conditions and/or results of the surgical procedure in which the intelligent surgical instrument is being used. Changing the at least one variable parameter is automated to improve patient outcomes. Thus, the intelligent surgical instrument can be configured to provide personalized medicine based on the patient and the patient's surrounding conditions to provide a smart system. In a surgical setting in which the intelligent surgical instrument is being used during performance of a surgical procedure, automated changing of the at least one variable parameter may allow for the intelligent surgical instrument to be controlled based on data gathered during the performance of the surgical procedure, which may help ensure that the intelligent surgical instrument is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Various embodiments of operating surgical instruments are described further in, for example, U.S. Pat. App. Pub. No. 2023/0096268 entitled "Methods for Controlling Cooperative Surgical Instruments" filed Oct. 5, 2021, U.S. Pat. App. Pub. No. 2023/0097906 entitled "Surgical Methods Using Multi-Source Imaging" published Mar. 30, 2023, U.S. Pat. App. Pub. No. 2023/0095002 entitled "Surgical Methods Using Fiducial Identification And Tracking" published Mar. 30, 2023, U.S. Pat. App. Pub. No. 2023/0101750 entitled "Surgical Methods For Control Of One Visualization With Another" published Mar. 30, 2023, U.S. Pat. App. Pub. No. 2023/0100698 entitled "Methods For Controlling Cooperative Surgical Instruments" published Mar. 30, 2023, U.S. Pat. App. Pub. No. 2023/0103005 entitled "Methods for Controlling Cooperative Surgical Instruments" published Mar. 30, 2023, and U.S. Pat. App. Pub. No. 2023/0098538 entitled "Cooperative Access Hybrid Procedures" published Mar. 30, 2023, which are hereby incorporated by reference in their entireties.

Data Pipelines

As discussed herein, data may be transmitted from one point to another point, such as during a performance of a surgical procedure on a patient. The data may be transmitted from a source system to a destination system using a data pipeline.

Figure 6A:
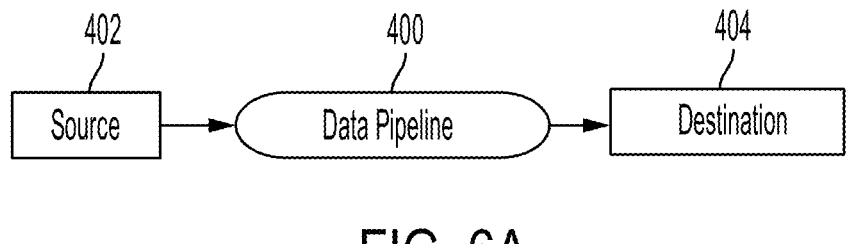
FIG. 6A is a schematic view of a data pipeline architecture.

As shown in FIG. 6A, a data pipeline 400 may move data from a source 402 to a destination 404 both physical and virtual (transient). In some data pipelines, the destination 404 may be called a "sink" or a "target." Any time data is processed between point A and point B (or between multiple points such as points B, C, and D), there is a data pipeline 400 between those points. In general, the data pipeline 400 can include a set of tools and processes, which may be referred to as "steps" or "processing steps" used to automate the movement and transformation of data between the source 402 and the destination 404.

In some embodiments, the source 402 and the destination 404 are two different elements, such as a first element of a surgical system and a second element of a surgical system. The data from the source 402 may or may not be modified by the data pipeline 400 before being received at the destination 404. For example, the source 402 may be one of the wearable sensing system(s) 111, the environmental sensing system(s) 115, the robotic system(s) 113, the intelligent instrument(s) 114, or the human interface system(s) 112 of the surgical system 102 of FIGS. 1 and 3 and the destination 404 may be the surgical hub 106 of the surgical system 102 of FIGS. 1 and 3. For another example, the source 402 may be one of the wearable sensing system(s) 111, the environmental sensing system(s) 115, the intelligent instrument(s)

114, or the human interface system(s) 112 of one of the surgical systems 102, 103, 104 of FIG. 1 and the destination 404 may be the surgical hub 106 of another one of the surgical systems 102, 103, 104 of FIG. 1. For yet another example, the source 402 may be one of the wearable sensing system(s) 111, the environmental sensing system(s) 115, the robotic system(s) 113, the intelligent instrument(s) 114, or the human interface system(s) 112 of the surgical system 102 of FIGS. 1 and 3 and the destination 404 may be another one of the wearable sensing system(s) 111, the environmental sensing system(s) 115, the robotic system(s) 113, the intelligent instrument(s) 114, or the human interface system(s) 112 of the surgical system 102 of FIGS. 1 and 3. For still another example, the source 402 may be one of the surgical systems 102, 103, 104 of FIG. 1 and the destination 404 may be another one of the surgical systems 102, 103, 104 of FIG. 1.

In some embodiments, the source 402 and the destination 404 are the same element. The data pipeline 400 may thus be purely about modifying the data set between the source 402 and the destination 404.

Figure 6B:
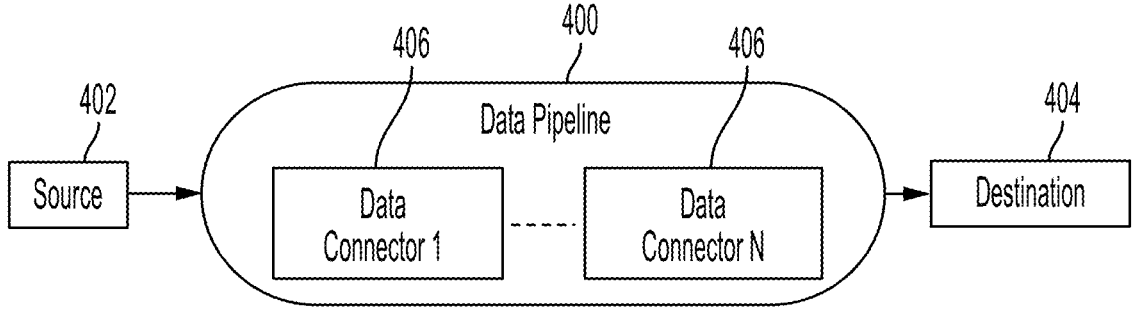
FIG. 6B is an expanded schematic view of the data pipeline architecture of FIG. 6A.

As shown in FIG. 6B, the data pipeline 400 may include one or more data connectors 406 that extract data from the source 402 and load the extracted data into the destination 404. A plural "N" number of data connectors 406 are shown in FIG. 6B. In some embodiments, such as embodiments in which extract, transform, and load (ETL) processing of data is performed, as opposed to extract, load, and transform (ELT) processing of data, data may be transformed within the data pipeline 400 before the data is received by the destination 404. In other embodiments, such as embodiments in which ELT processing of data is performed, as opposed to ETL processing of data, the one or more data connectors 406 may simply load raw data to the destination 404. In some instances, light transformations may be applied to the data, such as normalizing and cleaning data or orchestrating transformations into models for analysts, before the destination 404 receives the data.

The data pipeline 400 can include physical elements like one or more wires or can include digital elements like one or more packets, network traffic, or internal processor paths/connections. Flexible data pipelines are portions of the overall system where redundant paths can be utilized and therefore data, e.g., a data stream, can be sent down one path, parsed between multiple parallel paths (to increase capacity) and these multiple paths can be flexibly adjusted by the system as necessary to accommodate changes in the volume and details of the data streams as necessary.

The data pipeline 400 can have a small code base that serves a very specific purpose. These types of applications are called microservices.

The data pipeline 400 can be a big data pipeline. There are five characteristics of big data: volume, variety, velocity, veracity, and value. Big data pipelines are data pipelines built to accommodate more than one of the five characteristics of big data. The velocity of big data makes it appealing to build streaming data pipelines for big data. Then data can be captured and processed in real time so some action can then occur. The volume of big data requires that data pipelines must be scalable, as the volume can be variable over time. In practice, there are likely to be many big data events that occur simultaneously or very close together, so the big data pipeline must be able to scale to process significant volumes of data concurrently. The variety of big data requires that big data pipelines be able to recognize and process data in many different formats—structured, unstructured, and semi-structured.

In general, an architecture design of a data pipeline, e.g., the data pipeline 400 of FIGS. 6A and 6B, can include interconnectivity between a first smart device and a second smart device, e.g., the source 402 and the destination 404 of FIGS. 6A and 6B. Data generated in one source system (e.g., the first smart device or the second smart device) may feed multiple data pipelines, which may have multiple other data pipelines dependent on their outputs.

The interconnectivity between the first smart device and the second smart device may be on a common/shared network, e.g., LAN, Wi-fi, powerline networking, MoCA networking, cellular (e.g., 4G, 5G, etc.), low power wide area network (LPWAN), Zigbee, Z-wave, etc.

The interconnectivity between the first smart device and the second smart device may be on a structured network. Traditionally, structured peer-to-peer (P2P) networks implement a distributed hash table (DHT). In order to route traffic efficiently through the network, nodes in a structured overlay must maintain lists of neighbors that satisfy specific criteria. This makes them less robust in networks with a high rate of churn (e.g., with large numbers of nodes frequently joining and leaving the network). DHT-based solutions may have a high cost of advertising/discovering resources and may have static and dynamic load imbalance.

The interconnectivity between the first smart device and the second smart device may be via cooperative networking. Cooperative networking utilizes a system that is a hybrid of a P2P network and a server-client network architecture, offloading serving to peers who have recently established direct interchanges of content.

The interconnectivity between the first smart device and the second smart device may be exclusive. For example, the interconnectivity may be exclusive via Bluetooth. For another example, the interconnectivity may be exclusive via network isolation, such as by using path isolation, a virtual private network (VPN), or a secure access service edge (SASE). The path isolation may include a software-defined LAN (SD-WAN). SD-WANs rely on a software and a centralized control function that can steer traffic across a WAN in a smarter way by handling traffic based on priority, security, and quality of service requirements. The VPN may involve creation of an independent secure network using common/shared open networks. Another network (a carrier network) is used to carry data, which is encrypted. The carrier network will see packets of the data, which it routes. To users of the VPN, it will look like the systems are directly connected to each other.

For example, with interconnectivity between the first smart device and the second smart device being exclusive in a surgical context, an operating room (OR) may have a surgical hub and an established network from a first vendor. In order to secure against hacking or data leakage, the network may be an encrypted common network which the first vendor supplies keys from. A surgical stapler in the OR may be from a second vendor that is different from the first vendor and that does not have the keys from the first vendor. The surgical stapler may want to link to other device(s) it relies on for functionality but does not want data leakage. An advanced energy generator from the second vendor with an accompanying smoke evacuator may also be in the OR and may form their own private network, such as by piggybacking on the first vendor network to create a second encrypted VPN routing through the first vendor network as a primary network or by forming an independent wireless network for bi-direction communication between the advanced energy generator and the smoke evacuator. The surgical stapler may want to communicate with the advanced energy generator, e.g., so the surgical stapler may retrieve updated software from the advanced energy generator, receive tissue properties information from the advanced energy generator, log data for exportation, and receive energy from the advanced energy generator and apply the energy to tissue, but not want to communicate with the smoke evacuator, e.g., because the surgical stapler performs no smoke evacuation. The surgical stapler and a communication backplane of the advanced energy generator may therefore form an isolated network with only the surgical stapler (first smart device) and the advanced energy generator (second smart device) able to communicate via the isolated network and with the surgical hub able to manage the data pipeline between the surgical stapler and the advanced energy generator.

In general, one or more steps may be performed along a data pipeline, e.g., the data pipeline 400 of FIGS. 6A and 6B. The steps in the data pipeline may include data transformation, data augmentation, data enrichment, data filtering, data grouping, data aggregating, and running algorithms against the data.

The data aggregation may include segmentation of data into buckets (e.g., decomposition of a procedure into substeps), data fusion and interfacing, and mixing real-time data streams with archived data streams. Various embodiments of data aggregation are described further in, for example, U.S. Pat. App. Pub. No. 2022/0104896 entitled "Interactive Information Overlay On Multiple Surgical Displays" published Apr. 7, 2022, U.S. Pat. App. Pub. No. 2019/0206564 entitled "Method For Facility Data Collection And Interpretation" published Jul. 4, 2019, and U.S. Pat. App. Pub. No. 2024/0221937 entitled "Method For Advanced Algorithm Support" published Jul. 4, 2024, which are hereby incorporated by reference in their entireties.

In one embodiment, mixing real-time data streams with archived data streams may include, in a surgical context, pre-operative data/imaging evaluation. The evaluation may include displaying of static preoperative scan(s), overlaying of video with aligned 3D model, and registering a virtual view to a camera view.

In one embodiment, the display of static pre-operative scan may include alignment based on surgeon (or other HCP) position, for example, where the surgeon (or other HCP) is standing.

In one embodiment, registering the virtual view to the camera view may include identifying organs in a video and triangulating with camera location and/or getting a camera location in reference to a coordinate system. For example, during performance of a surgical procedure, a camera location may be acquired with respect to a trocar by 3D tracking of the trocar, camera insertion in the trocar (e.g., insertion depth and/or insertion angle, and/or determination of what trocar is being used for the camera. An example of insertion depth is a marking on a shaft of the trocar, such as on a graphical scale or a color gradient. Examples of insertion angle in a trocar are 3D trocar orientation and 3D angle of attack.

In one embodiment, the pre-operative data/imaging evaluation may include using a machine learning (ML) algorithm to reviewing preoperative scans of a patient to identify any abnormalities. A cloud-based source may be used for augmented reality (AR) using cloud-based data for surgical procedure planning.

In one embodiment, an ML algorithm may be used in an initial planning stage, e.g., initial planning for a surgical procedure to be performed on a patient. Preoperative scans may be used to facilitate surgical path planning. If the initial scans detect anomalies or diseased tissues, as analyzed by the ML algorithm, the anomalies or diseased tissues may be relayed to the surgeon for the upcoming surgical procedure and a new surgical task order may be suggested based on how previous surgeons handled these problems. The relayed information to the surgeon may also include a recommended inventory list to have on hand based on this initial improved surgical task order.

For example, during preoperative scans for a sleeve gastrectomy, a small hernia may be discovered. This hernia may be highlighted during the surgical planning step and the surgeon may be asked if the surgeon wants to include a hernial repair in the initial sleeve gastrectomy plan. Based on the surgeon's answer, the hernial repair will be added into the surgical task order for an affirmative surgeon answer and the overall inventory for this case will be updated to include relevant items for the hernial repair added into the surgical task order. During performance of the sleeve gastrectomy, a ML algorithm may be used to detect diseased tissue or surgical anomalies. If a diseased tissue is discovered, the diseased tissue may be highlighted on a screen, e.g., on a HID, and a cutting path/angle may be recommended to avoid the tissue or make the tissue state more manageable. These recommendations may be based on how surgeons previously, successfully, handled these situations. If a surgical anomaly is discovered, the system may either automatically update the task order or require the surgeon to give a verbal command (or other command) to update the task order and highlight the required additional inventory on the circulators screen. For foreign bodies (such as bougies) that may be discovered, the foreign body may be highlighted on the screen and a cutting path may be included to provide an ample margin around the foreign body, assuming the foreign body is anticipated. If the foreign body is not anticipated, the foreign body may be highlighted to draw the surgeon's (and/or other HCP's) attention to it.

In one embodiment, the pre-operative data/imaging evaluation may include a cloud comparison of scans periodically taken through time for anatomic changes of that time to indicate possible operative complications. A cloud-based source may be used for augmented reality (AR) using preoperative scans to enhance return surgeries.

Looking at a difference between current and previous surgical scans may help inform the surgeon and/or other HCP and improve patient outcomes. This information can be used in various ways, for example for disease detection, informing surgical task planning, and/or informing previous surgical success and healing.

With respect to disease detection, current and historical scans can be used to determine if various disease states or abnormalities have evolved between surgeries. One case where this could be particularly useful is cancer detection. If a scan initially picks up an abnormal growth for a patient but the patient's HCP decides that it is benign but decides to flag it for caution, a follow-up scan nay confirm that the abnormality is benign or not. The scan may also automatically highlight areas of concern (tissue growth) that were not flagged by the HCP initially but could be areas of concern.

With respect to informing surgical task planning, information about previous surgeries (e.g., potential areas of scare tissue, previously seen difficult tissue, etc.) can help facilitate surgical step and path planning. This information can also be used during the surgery to display areas of scarring, changes of tissue from previous surgeries that might need to be examined, foreign bodies, and/or new adhesions.

With respect to informing previous surgical success and healing, data from various scans over time can be used to determine how successful patients were recovering or had recovered from previous surgeries. This information may be used by surgeons (and/or other HCPs) to help plan future procedures, assess previous work, and/or facilitate quicker patient recovery.

Data development may be performed as a step in a data pipeline and may include one or more of data modeling, database layout and configuration, implementation, data mapping, and correction.

Various data may be communicated using a data pipeline, e.g., the data pipeline 400 of FIGS. 6A and 6B, such as data from a local data source, data from a remote data source, and synthetically generated data.

Data from a local data source may include data collected by, used by, or resulting from the operation of aspects of the local data source, e.g., data gathered using a sensor (e.g., temperature data gathered using a temperature sensor, force data gathered using a force sensor, pressure measured using a pressure sensor, etc.), still and/or video image data (e.g., data gathered by a camera, etc.), operational parameters of a surgical instrument (e.g., energy level, energy type, motor current, cutting element speed, etc.), surgical instrument identification (e.g., instrument type, instrument serial number, etc.), etc.

Data from a local data source may have metadata, which may reflect aspects of a data stream, a device configuration, and/or system behavior that define information about the data. For example, metadata may include an auxiliary data location that is shared by two interconnected systems, e.g., first and second robotic systems, etc., to create a single "brain" instead of two distinct ones. Each of the interconnected systems may creates a copy of its memory system and introduce it to the combined system or "collective. Both of the interconnected systems may now use this new area for data exchange, for uni-directional communication, and to directly command control systems. The new combined system may become primary and the individual robotic system's memory areas may become secondary memory areas until the systems are "unpaired," e.g., are no longer interconnected.

Data from a local data source may include a data stream that is monitored by at least one other system. In this way, data collected by, used by or resulting from the operation of aspects of one system may be sourced to another system (the monitoring system).

In one embodiment, application programming interfaces (APIs) may be used to communicate data from a local source.

In one embodiment, data may be communicated from a local source in response to occurrence of a trigger event. In one embodiment, the trigger event is a digital trigger event. For example, in a surgical context, the trigger event may be a surgical instrument changing orientation after being in a predetermined static position, such as when the surgical instrument "wakes up." For another example, in a surgical context, the trigger event may be a system's power or signal interruption, e.g., communicating data after the interruption has been resolved. For yet another example, in a surgical context, the trigger event may be a change in system status, capacity, or connectivity. For still another example, in a surgical context, the trigger event may be quality, calibrations, or conversion factors of a surgical instrument.

Data from a remote data source may include data collected by, used by, or resulting from the operation of aspects of the remote data source. One example of a remote data source includes a database, such as a relational database or an NoSQL database. Examples of data in a relational database relevant in a surgical context can include inventory, sterile services process status, billing code, patient records (PHI), and previous procedure data.

One example of data from a remote data source, in a surgical context, includes a procedure plan, e.g., a plan for a surgical procedure to be performed on a patient. The procedure plan data can include, for example, instrument selection, port placement, adjuncts needed for devices, OR timing and local imaging needs, procedural steps, staff number and skill composition, and patient positioning.

Another example of data from a remote data source, in a surgical context, includes pre-operative imaging, such as a CT full body scan, external ultrasound, MRI, etc.

Another example of data from a remote data source includes software parameter updates, such as software parameter updates streaming from a cloud computing system. The software parameter updates can include, for example, original equipment manufacturer (OEM) updates to a device's operational aspects, e.g., updated basic input/output system (BIOS) controls, calibrations, updates on capabilities (e.g., recalls, limits/expansion of use, indications, contra-indications, etc.), etc.

Another example of data from a remote data source includes gold standard of care or outcomes improvement data, such as gold standard of care or outcomes improvement data from a cloud computing system. Gold standard of care or outcomes improvement data can include, for example, improved techniques of device use and/or device combinations.

In one embodiment, Apache® Hadoop®, which is an open source software framework, may be used for distributed processing of data across computer systems.

Examples of types of synthetically generated data may include synthetic text, media (e.g., video, image, sound, etc.), tabular data, and calculated continuous stream of data. The calculated continuous stream of data may be randomly generated (bracketed by extremes thresholds) or may be based off another stream or real continuous data stream that is modified to fit the stream limits of the expected synthetic stream. Reasons for using synthetically generated data can include for training data streams, because of missing data from an expected system that would otherwise draw a device error but is not relevant to the operation of the device or other dependent device, for data streams designed to verify the operational of the transforms or mathematic algorithms, for data streams intended to either verify security or prevent fraud/inauthenticity, for consecutive timing data for redaction of real-time from the relational data of the systems, for creations of trending data for replacement of legal compliance regulated data streams (e.g., either they produce datasets from partially synthetic data, where they replace only a selection of the dataset with synthetic data), and/or for a sudden but anticipatable/explainable change in a data source's feed which is being used as a closed loop control for a destination.

For example of use of synthetically generated data in a surgical context in which a surgical procedure is being performed on a patient, a $PO_2$ sensor (data source) on the patient's finger may be being used as a means for controlling a closed loop feed or $O_2$ through a ventilator (data destination). The ventilator also has an internal closed loop on $CO_2$ outlet concentration, but since $O_2$ blood saturation is the desired fixed relationship to $O_2$ supplementation level, the ventilator is using the $PO_2$ sensor from the patient monitoring system. There may be an abrupt change in the $O_2$ level as measured by the $PO_2$ sensor. The ventilator has two choices: ether switch to the trailing indicator or $CO_2$ which has not had an abrupt change or examine other data sources to try to explain the $O_2$ shift. When compared to the patient's core body temperature measure it may be discovered that the patient's temperature has dropped across a 1.5° C. below normal threshold that usually induces vasoconstriction limiting blood flow to the body's extremities. The $PO_2$ measure by its metadata is known by the ventilator to be a finger monitor and therefore on an extremity. Further comparison over time may show the $O_2$ measure fairly constant before the shift and then fairly constant after the shift as well, reinforcing the idea that this is the vasoconstriction that induced the shift. The ventilator may then create a synthetic data stream based on the shift data pattern and behavior that compensates for the vasoconstriction shift so the ventilator can continue on the primary linked feeds but using a modified synthetic or "calculated" data stream based of a real stream. For example, current body temperature control systems, such as a Bair Hugger™ device, are open-loop user settable heat gradient controlled systems but are affected by local temperature and environment.

Adjusting Data Pipeline Mapping

In various aspects, the present disclosure provides methods, devices, and systems for adjusting a data pipeline mapping, such as the data pipeline 400 of FIGS. 6A and 6B. In a surgical context, adjusting data pipeline mapping may allow for a data pipeline to be altered during a performance of a surgical procedure on a patient so data may flow more efficiently and thus help ensure that data is received at an intended destination in a timely fashion so the data may be used properly and promptly.

Adjusting data pipeline mapping may include network management and interaction. In one embodiment, the network management and interaction may include data pipeline architecture and configuration. The data pipeline architecture and configuration may include changing data pipeline mapping between a source and a destination, e.g., mapping of the data pipeline 400 of FIGS. 6A and 6B between the source 402 and the destination 404, based on needs of the data being transferred. In one embodiment, the changing of the data pipeline mapping may include, during performance of a surgical procedure, altering data stream pathways through the system from collection to user display or use based on a parameter of the data, the surgical procedure, or data collected outside of what is being used. These alterations can change the transforms based on when the data is transformed, where the data ends up, and whether or not it ends up in only one location or multiple locations. The needs may include size of the data, transfer rate of data, criticality of the data, and bandwidth capacity of the systems. The adaptation may result in the physical limitation of either system.

The data pipeline architecture and configuration may include dynamic/adaptive data pipeline mapping that can change relationships of the networks, e.g., changes in destinations or sources, parallel versus serial data pipelines, data rates, data resolution, data transmission frequency, and time based aspects of transfers. In general, data pipelines may be considered a road, flow management may be considered traffic on the road, and a data pipeline route may be remapped because of the needs of the data traffic.

Various types of data adaptation may be performed in dynamic/adaptive data pipeline mapping. One example of the type of data adaptation that may be performed in dynamic/adaptive data pipeline mapping includes selective use of parallel pipes to handle increased bandwidth/magnitudes of data depending on the situation. For example, selective use of parallel pipes may include switching from pre-transformed, e.g., FPGA transformed data from the source, to raw data in order to enable post procedure alternative analyses which would require extra ancillary or bigger unprocessed data being transported in the same manner.

Another example of the type of data adaptation that may be performed in dynamic/adaptive data pipeline mapping includes re-ordering sequence of operations. For example, re-ordering sequence of operations may include redirecting an order of the data pipelines to re-orient the steps the data is processed through, e.g., storage of the data before or after the data is utilized.

Another example of the type of data adaptation that may be performed in dynamic/adaptive data pipeline mapping includes balancing of data pipelines with a throughput of the overall system. The balancing of data pipelines may include a system performing the data adaptation, e.g., a surgical hub or other system, may request some systems lower their data stream volume either through more local transformation or through sampling rate or resolution rate reduction. The balancing of data pipelines may result in a throttling of data rate due to changing the type/magnitude of the needed data while not changing the pipelines.

Another example of the type of data adaptation that may be performed in dynamic/adaptive data pipeline mapping includes data transmission modification. the data transmission modification may include physical transmission changes, which may include adjustment of the physical layer based on signal strength; data transmission speed, which may include speeding up data transmission on wireless networks at the expense of additional power and/or opening up additional bandwidth at the potential risk of data loss; modification of data packets, which may include a reduction in overhead by reverting back to status updates only and not floating point; and/or modification of data transmission, which may include removing handshaking, e.g., ACK/NACK packets, and checksums to reduce data.

Another example of the type of data adaptation that may be performed in dynamic/adaptive data pipeline mapping includes communication of timing of protocol changes. The communication may be via a secondary mechanism or a primary mechanism. With the secondary mechanism, messages may be sent over a different method to indicate the current protocol being used. For example, a digital IO line may be configured 'high' for 115200 baud rate and 'low' for 9600 baud rate. With the primary mechanism, messages sent over the primary method 'count down' a protocol change. For example, one of the messages may indicate "In 3 messages we will change . . . "

In dynamic/adaptive data pipeline mapping, an importance of data versus resource level, e.g., the capacity of the data pipelines and ability to re-task certain data pipelines) may be used in redirecting portions of data stream volume based on circumstances.

In one embodiment, the redirecting may be based on situational adaption. For example, as non-monitored by the user wavelength data from an advanced imaging system detects, e.g., during performance of a surgical procedure, an unexpected or abrupt shift in a parameter, such as reflectivity, it may be requested to the reviewing smart system if it should send untransformed data, which is generally larger or bulkier data, rather than the sole monitored data stream for later or expanded investigation. For further example, as a multispectral and ultrasound flexible endoscopy system approaches a bile duct of a patient during performance of a surgical procedure on the patient, a surgical hub (or other system performing the redirecting) may request (e.g., request adaption) the imaging to start supplying untransformed data rather transformed data so the surgical hub can collect more information about the surgical site that the surgeon and/or other HCP is using. Thereafter, when the patient has a post-operative task of recovery or has a complication, the surgeon and/or other HCP can go back to the untransformed data and review other aspects of the organs, disease state, and implications. For example, the reflectivity of the multispectral light may identify local infection versus inflammation, both of which would present as aggravating post situations but would require completely different treatment, e.g., antibiotics versus anti-inflammatories, and therefore the secondary collected data may be used to determine treatment without re-opening the patient.

In one embodiment, the redirecting may be based on requested adaption. The requested adaptation may include a surgical hub performing the redirecting, or other system performing the redirecting, realizing the systems are approaching more critical anatomy or parts of a surgical procedure being performed on the patient and, in response, requesting the projection smart system to start sending untransformed data rather than transformed data. For example, a surgeon and/or other HCP may be mobilizing a colon of the patient for a transection of cancer and accidentally allow a hot blade to contact tissue outside of a current field of view shown on a monitor, such as a HID, but within the full field of view of available CMOS arrays and/or other image sensor. Thereafter, revisiting the more comprehensive untransformed data may indicate a perforation that could drive the surgeon and/or other HCP to re-open the patient days post-op rather than merely try to treat the patient with antibiotics.

In one embodiment, the redirecting may be based on prioritization of data and/or data sources. The prioritization may include adding additional data lines and/or using a predefined pipe with dynamic prioritization, e.g., IP servers with guaranteed prioritization for certain processes.

In dynamic/adaptive data pipeline mapping, certain circumstances may require data pipeline mapping adjustment. The circumstances may include at least one of data stream mapping changes, identification of questionable data integrity, video compression/decompression, and prioritization.

Re-mapping because of data stream mapping changes may include real-time transfer of the data and post (or out of real-time) deposition of the data for later artificial intelligence (AI), ML, or storage means.

In one embodiment, the circumstance triggering a data stream mapping change may include a new data stream being available to connect to a data pipeline. The re-mapping may include connecting the new data stream to the data pipeline so data from the new data stream may be shared by being transmitted via the data pipeline.

In one embodiment, the circumstance triggering a data stream mapping change may include a device being on, and thus be available for data gathering and transmission, during performance of a surgical procedure but have one or more data streams not be needed in the surgical procedure. The re-mapping may include connecting the one or more data streams to the data pipeline when the one or more data streams become needed. For example, during surgery, a laparoscopic camera may on but not needed. The laparoscopic camera may thus only record and transmit a decimated/lower definition for context until high density data is required, at which time re-mapping may occur to allow for the HD data on the data pipeline. For further example, the laparoscopic camera may have multiple CMOS arrays and/or other image sensors, and thus essentially have multiple cameras. In some cases only one of the cameras may be in use while the other is idle. The idleness may be related to reducing the resolution of spectral frequencies the laparoscopic camera is collecting and therefore minimizing the size of the data pipeline needed to transfer the camera-created data. Only utilizing the entire system when necessary may minimize other feeds to make room for the data streams within the data pipeline.

In one embodiment, the circumstance triggering a data stream mapping change may include an image being blurry. A device may have an ability to determine if an image is blurry, e.g., because a camera that gathered the image is moving, and reduce the resolution/throughput of the camera to reduce system load. For example, a motion detection system on the camera may determine when to de-prioritize data quality and/or may reduce the data quality unless at least one user (e.g., surgeon and/or other HCP) is focused on, e.g., looking at, a display, e.g., HID, showing the image through face/eye recognition, e.g., as detected by camera(s) in a surgical theater in which the display is located. Various embodiments of determining that a user is focused on a display are described further in, for example, U.S. Pat. App. Pub. No. 2022/0104896 entitled "Interactive Information Overlay On Multiple Surgical Displays" published Apr. 7, 2022, which is hereby incorporated by reference in its entirety.

In one embodiment, the circumstance triggering a data stream mapping change may include occurrence of an adverse surgical incident during a performance of a surgical procedure on a patient. Examples of adverse surgical incident are bleeding, air leaks, collateral thermal damage, and inadvertent adjacent tissue damage. For example, occurrence of an adverse surgical incident may mean a surgeon and/or other HCP prefers to look at a wider camera angle than what the current digital zoom is focused on to allow visualization of a wider area for assessment of the adverse surgical incident and determining any redress actions. For another example, when an adverse surgical incident occurs, then the system may want to collect information outside of a camera's current field of view in order to better proved context for later diagnostics. For another example, when an adverse surgical incident occurs by a hot blade energy device moving outside of a camera's current field of view while still hot, it may be useful to track any inadvertent tissue contacts while the currently non-visualized hot blade energy device could be capable of still damaging tissue.

In one embodiment, the circumstance triggering a data stream mapping change may include multi-spectral data being needed even if, during performance of a surgical procedure on a patient, a surgeon and/or HCP is not currently using the multi-spectral data to visualize some overlay aspect. For example, if an energy device is used on tissue of the patient, an IR spectrum may be used to monitor steam expansion and therefore collateral damage of tissue caused by the use of the energy device. For another example, if a ultrasonic device is used on tissue of the patient, a blade at a tip of the ultrasonic device may be hot and cause inadvertent damage if the tip is laid on tissue before the blade cools. An IR spectrum may be used to track device tip temperature. Many spectrums other than the IR spectrum may be used to monitor relative reflectivity of tissue which may be used to mark damage, infection, or irregularities that were there from the beginning, e.g., pre-existing and thus not caused during the surgical procedure, or occurred during surgical intervention. Any spectrums used may help with diagnostics post-surgery if a complication were to result.

In one embodiment, the circumstance triggering a data stream mapping change may include structured light being useful in collecting information beyond its normal intended use. Structured light may be used during performance of a surgical procedure to track organs, surfaces, or surgical instruments even when not being directed by a surgeon and/or other HCP for distance or volume measurements. These tracking aspects may be used to maintain situational awareness of device(s) and organ(s) as they are outside of a current field of view and may be used to highlight to the surgeon and/or other HCP if something could require their attention because something important is occurring outside of the field of view. These tracking aspects may be used to create a directionality icon with the field of view to direct the surgeon and/or other HCP if they are interested in looking.

In one embodiment, the circumstance triggering a data stream mapping change may include wanting untransformed data recorded rather than normal transformed data in the pipeline. Context or metadata is lost when a data stream is transformed at a source before communication to another system via a data pipeline. If the data becomes suspect or questionable, the source may be asked, e.g., by a destination of the data, to send all the collected data as collected rather than a transformed set.

In one embodiment, the circumstance triggering a data stream mapping change may include an internal network event. Examples of an internal network event include a portion of a system going down or requiring rebooting, thermal dissipation of heat probably caused from over use of main processor chips like video cards or primary processors, and data loss.

When an internal network event includes a portion of a system going down or requiring rebooting, re-mapping may include a dynamic reconfiguration of the data pipeline architecture based on power or system status. The power or system status may be a planned event, such as events where the system has a priori knowledge of how its system states will be impacted, or an unplanned event, such as events where the system does not have a priori knowledge of how its system states will be impacted. For example, a planned event can be a clinical user initiating a turn-off sequence on a device, and the system is able to gracefully shutdown. For example, an unplanned event can include a device being plugged into a wall outlet using an AC cord. The AC cord is subsequently and unexpectedly pulled out from the wall outlet, resulting in a system shutdown.

The system performing re-mapping may need to reconfigure portions of its data pipeline based on the status of the system. In order to accomplish this, the system may have either pre-existing accommodations to allow for a dynamic restructuring (re-mapping), or the system may attempt to establish contemporaneous accommodations for re-structuring (re-mapping). These systems may allow for all, portions of, or mission critical functionality of the system to remain active during changes in a system status.

Mission critical portions of a data stream may be duplicated in a more basic form through an available or recently freed up alternative data pipeline which may be isolated from the portion of the network requiring rebooting. Once the mission critical portions are rerouted the portion that is in trouble may then be isolated from the primary network and then restarted and then re-synchronized.

The system performing re-mapping may utilize a safety processor or secondary backup system that may be re-tasked to handle mission critical operations (like minimal visualization processing) in a portion of the overall surgical hub or system that can be fully electrically isolated and operated away from the rest of the system. The rest of the system may then be re-started and re-initialized and, once operational, the safety processor or secondary backup system may then be re-tasked back to its original function.

The system reconfiguring portions of its data pipeline may reconfigure according to pre-existing architectural accommodations or to contemporaneous architectural accommodations.

For pre-existing architectural accommodations, the system has been inherently designed to accommodate different potential failure modes, based on pre-existing or pre-identified potential failure modes. For example, a system which processes laparoscopic serial digital interface (SDI) video feed data and then outputs an overlaid video feed solution to a user (e.g., surgeon or other HCP) may have a mechanical bypass switch installed. The bypass switch will automatically take over in the event of a power failure. While all overlays will be lost, the raw laparoscopic video feed would be preserved for the user.

For contemporaneous architectural accommodations, the system may have been designed with an architecture that allows for redundancy or mitigations to be implemented but does not necessarily specify specific accommodations. For example, a complex electrical video switching system may route video feeds from multiple sources (such as laparoscopic, overhead camera, etc.) to multiple other destinations, including laparoscopic monitors, staff monitors, etc. If a single source is interrupted, there may be no designed-in explicit mitigation, but the system may use alternative fallback mechanisms (last-used, highest priority designation) to determine how video should be routed to monitors going forward.

When an internal network event includes thermal dissipation of heat probably caused from over use of main processor chips like video cards or primary processors, the re-mapping may include changing one or more data pipelines to re-balance temperature and thermal conditions. In general, adapting a ratio of collecting systems versus systems using data transform may minimize thermal overload.

A temperature imbalance may trigger re-mapping to re-balance temperature and thermal conditions. The temperature imbalance may be caused by a blocking of airflow. Capital equipment is often relocated in an ad-hoc manner within an operating room. Multiple fans and/or vents may exist on a piece of capital equipment. As a result, the situation could arise that a portion of available vents are blocked.

The temperature imbalance may be caused by component failure. Capital equipment may often have numerous fans located within the equipment to provide adequate cooling. If a fan was to fail in the middle of a surgical case, e.g., during performance of a surgical procedure on a patient, it may be preferred that the equipment continue to run in a reduced manner (soft failure) as opposed to a complete shutdown (hard failure). The loss of a single fan may imbalance the cooling within the unit as well.

The temperature imbalance may be caused by exceeding rated ambient temperature. Capital equipment is often developed to operate in a specific ambient environment, such as within an air conditioned room. However, microclimates can exist even within an air conditioned room, such as within a rack with other equipment, or due to other adverse conditions within a hospital system, such as loss of air conditioning. Capital equipment may be co-located with other equipment that causes it to take on a large amount of thermal load, e.g., by being co-located in a microclimate or an area with air conditioning loss.

The temperature imbalance may be caused by fault conditions of a processor. A processor that was allocated to the system may be damaged and/or removed. In order to achieve minimum system performance with the damaged/removed processor, the system overclocks or speeds up the remaining allocated processor(s). This eventually may result in overheating.

Rebalancing temperature and thermal conditions may include rebalancing for overall system compensation. Capital equipment may be designed with numerous components (e.g., CPU, GPU, etc.), which have corresponding amounts of headroom in their designs. These pieces of equipment may additionally have different ratings in a design. In this case, if the overall system is starting to approach the design limits, processing may be rebalanced to continue to maintain a minimum amount of thermal headroom. This can also apply to a system composed of multiple pieces of equipment within a room.

The re-balancing for overall system compensation may include intentionally unbalancing a balanced system to compensate for thermal stress. For example, a piece of capital equipment may be designed with a CPU which has a thermal cutoff of 105° C. and a GPU with a thermal cutoff of 125° C., with a design constraint of maintaining 40° C. of headroom at all times to preserve life span. This creates effective limits of 65° C. for the CPU and 85° C. for the GPU. The capital equipment may be placed in a rack with other equipment and may start to experience temperature creep. As a result, temperatures for the CPU may start to approach 60° C., with the GPU also at approximately 60° C. Since the GPU has considerable headroom remaining, the system may re-balance performance needs, lowering the CPU temperature to 50° C., although the GPU temperature rises to 70° C. However, both systems are now at approximately 15° C. from their associated cutoff.

Rebalancing temperature and thermal conditions may include rebalancing for localized system compensation. A localized section of the system may be experiencing thermal stress, and the system may rebalance to compensate for that.

The re-balancing for localized system compensation may include intentionally balancing an unbalanced system to compensate for thermal stress. For example, a piece of capital equipment may be designed with a CPU which has a thermal cutoff of 105° C. and a GPU with a thermal cutoff of 125° C., with a design constraint of maintaining 40° C. of headroom at all times to preserve life span. This creates effective limits of 65° C. for the CPU and 85° C. for the GPU. The capital equipment is operating with a nominal temperature of 40° C. on all components. However, the capital equipment may experience a fan failure in the CPU section and, as a result, temperatures start to shift internally to the CPU section. As a result, without any action, the GPU sees some indirect impact, such as increasing by 5° C., and the CPU sees a significant increase, e.g., increase of 30° C. This significant increase causes the CPU temperature to significantly rise, e.g., reach 70° C., and be above the CPU effective temperature limit and the GPU temperature to rise, e.g., reach 45° C. Since the CPU's temperature exceeds the desired temperature of 65° C. for the CPU, processing may be offloaded from the CPU to the GPU to bring the system back to thermal equilibrium, with both systems now operating at approximately 57.5° C.

Rebalancing temperature and thermal conditions may include correction of imbalances in system performance and/or processors. In an ideal system, all processors are equally balanced to allow for distributed processing to occur in any of the processors allocated to it. However, in practice, there may be discrepancies between different processors or the capabilities that they present.

When an internal network event includes data loss, a system may change or re-balance data throughput or speed with redundancy to insure minimal risk of lost data in transit or in safety of operation of the closure loop controlled system on a data stream from another system. Data flow(s) configuration may thus occur while changing from transformed to less transformed data streaming.

In such re-mapping, data integrity may be improved by using bit matching or other methods to ensure redundancy while minimizing the cost of resources to the transit or using system. Standard RAID levels may be used, e.g., RAID 0—striping (fastest), RAID 1—mirroring (most redundant), RAID 5—striping with parity (partial redundancy with partial speed), RAID 6—striping with double parity, and RAID 10—combining mirroring and striping (when size of the system is less important).

In such re-mapping, the system has lost the necessary capabilities to provide redundancy. As a result, resources may be allocated to other functions where they can be more useful, such as improved speed.

Figure 7A:
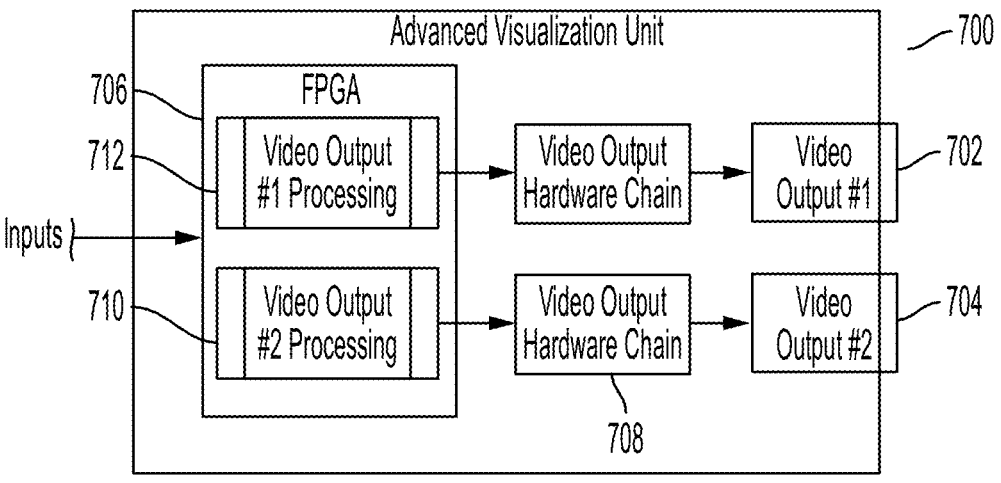
FIG. 7A is a schematic view of one embodiment of an advanced visualization unit in a nominal state.
Figure 7B:
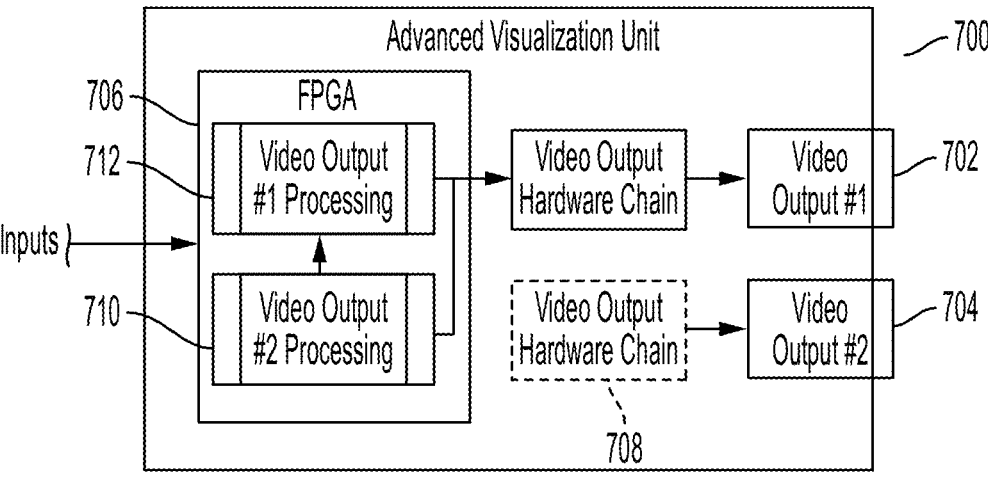
FIG. 7B is a schematic view of the advanced visualization unit of FIG. 7A in a reallocated state.

FIGS. 7A and 7B illustrate one embodiment of a system changing or re-balancing data throughput or speed with redundancy. FIG. 7A shows a nominal state of an advanced visualization system (also referred to herein as an "advanced visualization unit") 700 that may provide two video outputs 702, 704, e.g., to support either redundant operations or for 3D imaging. However, both video outputs 702, 704 may be connected to the same FPGA 706 to provide video processing. A hardware fault may be detected in an output chain 708 for the second video output 704, but not within the FPGA 706 itself. Since it would no longer be useful to keep resources dedicated to the second video output 704, the FPGA 706 may be able to reallocate portions of its processing and the associated internal pipelines to support any processing to be done in the first video output 702. FIG. 7B shows FPGA resources 710 for the second video output 704 reallocated to FPGA resources 712 for the first video output 702.

As mentioned above, an adaptation of data pipeline architecture redirection pathways may be due to identification of questionable data integrity. In other words, data integrity may be utilized as a means to determine the need for re-mapping of a data pipeline.

A triggering threshold that causes the re-mapping of a data pipeline may be one or more of corruption of data, coherence of data, cohesion of data, trustworthiness of data, and ability for a system to identify a more appropriate pipeline configuration.

Corruption of data may occur, for example, because of a sensor. Bounding conditions of realisticness of sensor data (limit settings, such as temperature limits) may indicate that the data has been corrupted. i.e. temperature limits. For example, the sensor may be broken/damaged. For another example, it may be observed that sensor data is being "listened to/snooping" from external source(s).

Corruption of data may occur, for another example, because of data decompression, such as from cyclic redundancy check (CRC) failure or digital-to-analog converter (DAC) bit compressing. Data decompression may be identified using byte size limits and/or conversions timing limits.

Incoherence of data may occur when a data flow is no longer logical or consistent.

Incoherence of data may occur when signal conditioning fails, such as from damaged hardware filtering or operational amplifier (opamp) gain shifting. Signal conditioning failure may be identified using voltage setting limits.

Incoherence of data may occur when data conversion/compression/transformation fails, such as from CRC failure or analog-to-digital converter (ADC) bit compressing. Data conversion/compression/transformation failure may be identified using byte size limits and/or conversions timing limits.

Incoherence of data may occur due to data utilization error, such as a data type mismatch (e.g., temperature versus speed, etc.), a data format mismatch (e.g., integer versus string, etc.), or a data unit mismatch (Celsius versus Fahrenheit, etc.). A data utilization error may be identified using try . . . catch error handling and/or human intervention.

Lack of data cohesion may occur when multiple data streams that were paired or aligned now appear to be unaligned, out-of-sequence, or asymmetric.

Data may be untrustworthy due to faulty signal transmission, such as poor signal strength, snooping, or memory starving. Untrustworthy data may be identified by send/receive timing limits.

The ability for a system to identify more appropriate pipeline configuration may be, for example, a surgical hub receiving data from a sensor (or other source) that the surgical hub does not need but knows a different system needs but may not have. The surgical hub may forward that data on to the system that needs the data or may lead an effort to create a data pipeline between the system that needs the data, e.g., the destination, and the sensor (or other source).

The ability for a system to identify more appropriate pipeline configuration may be, for another example, a visualization system identifying a device that has data streams and needing to establish new data pipeline(s) for the device as a source and/or destination.

Reaction to a triggering threshold that causes the re-mapping of a data pipeline may be bypassing of intermediate stops, stations, or junctions the data passes through; redirection of paths to take different physical wiring connections or pathways; redirection to an independent switching array to control the data architecture; and/or selective shutoff/turn on (partial or full). The selective shutoff/turn on may include pausing accessibility of a system that was in use during performance of a surgical procedure, system timeouts (source or sink), procedural step criticality, preserving a full dataset but sending only a required subset of data on a data pipeline, capacity/capability reduction to maintain pipeline stability, and/or adjust device pipelines when introduced into or removed from the surgical field.

As mentioned above, prioritization may require data pipeline mapping adjustment. The prioritization may be based on a usefulness of secondary information, criticality of a particular data to a particular surgical step being performed in a surgical procedure, and/or variability of the data (e.g., one stream is transmitting fair consistent output data and only needs to be prioritized if that changes). For variability of the data, a threshold range may be used to define when something important happens.

In dynamic/adaptive data pipeline mapping, a data pipeline may need to be reconfigured while the data pipeline is transferring data. In such a scenario, the re-mapping may include determining when and to what extent the data pipelines require re-tasking and dynamically adapting an actively used data pipeline to maintain continuity of data.

Determining when and to what extent the data pipelines require re-tasking may include determining a magnitude of changes to a data pipeline map due to changing needs of the data. In one embodiment, determining the magnitude of changes may include seamlessly having data continuity at an appropriate data throughput rate by identifying a trigger event to switch data pipelines. The trigger event may be, for example, a broadcast of an interrupt to distribute the next data pipeline configuration prior to additional data frames. For another example, the trigger event may be a control/configuration data pipeline dedicated to managing a flow of data streams. For yet another example, the trigger event may be an advertising channel for each data pipeline that creates network awareness for other data pipelines. For still another example, the trigger event may be an automatic look for a new available data pipeline if an original, e.g., currently existing, data pipeline is disconnected.

The data pipeline chosen to switch to may be based on pipe priority. The pipe priority may be based on one or more of available infrastructure, e.g., determination of available data pipelines for data streams (direct or indirect); data pipeline congestion, e.g., ability to measure data pipeline congestion through software or electrical means; and risk.

In one embodiment, determining the magnitude of changes may include non-seamlessly having data continuity at an appropriate data throughput rate by identifying a trigger event to switch pipes. The trigger event may be, for example, pausing data transferring to allow for data pipeline re-configuration to commence. For another example, the trigger event may be buffering data until idle time is available is another option. For yet another example, the trigger event may be non-deterministic single-point data (only latest data matters) with missed datasets being considered as not important.

In one embodiment, determining the magnitude of changes may include determining when to shutoff/re-configure a data pipeline by creating a duplicate data stream on a new data pipeline configuration while the new data pipeline connection is stabilizing or by determining what data frequency for each data pipeline is critical to procedure. With respect to creating a duplicate data stream, one example is a WIFI connection dropping and cellular (e.g., 5G or other cellular protocol) picking up after a certain reduction in signal strength.

Also with respect to creating a duplicate data stream, since reconfiguring for bandwidth or volume issues needs more resources before it can use less resources for the extra capacity for a duplicate data stream, other may be adjusted streams to accommodate the monetary need. If resources are constrained, the control system (e.g., a surgical hub or other system controlling the reconfiguring) may de-escalate priority, frequency, or breath of other data feeds to enable the parallel portion of the switching stream. This would result in a temporary reduction in resolution, frame-per-second, accuracy, or even accessibility of some other data streams that are not currently being used for a smart system to smart system closed loop or relevant to a user (e.g., HCP) in real-time. The reduced data streams may result in one or more of the smart systems being instructed to operate in an open loop manner until the reduced data stream could be restored. Loss of the data may be mitigated by instructing the send system (e.g., source) to send the data to an offline storage buffer or to buffer the data internally until resources are again available for transmission after the switchover is complete.

In one embodiment, determining the magnitude of changes may include monitoring a level of data throughput (or a proxy for a level of data throughput) achieved on a data pipeline as an indicator for when to transition to a new data pipeline. For example, a smart system being used in a surgical procedure may be connected wirelessly to a battery-operated smart stapling device (battery-operated intelligent surgical stapler). As the battery-operated smart stapling device starts to consume battery and reaches a critical threshold, its RF transmit power may be reduced, and frequency of data transmission may be further reduced as well. In addition, the loss of RF transmit power may reduce a clarity with which messages are received, sometimes requiring a second message to be transmitted. As a result, this can be a trigger to switch to a new device or battery system for the smart stapling device.

Potential metrics to monitor in monitoring a level of data throughput for when to initiate a transition include one or both of data upload/download speed and proxies for data throughput. For monitoring of data upload/download speed, when a data upload speed or download speed drops below a certain range, transitioning to an alternative data pipeline may be determined to be appropriate. Similarly, when a new data pipeline with higher speed becomes available, the system controlling the reconfiguring may transition to that new data pipeline.

One example of a proxy for data throughput is received signal strength indicator (RSSI), e.g., RF signal strength, which includes monitoring of a distance of a transmitter by a receiver or vice versa for understanding what a likely corresponding data throughput would be. As distance between a wireless transmitter and a receiver increases, the likelihood of an error in receipt of data increases as well. This reduces the likelihood of data being received in a consistent and correct manner.

Another example of a proxy for data throughput is rate of change of RF signal strength, which includes monitoring of changes in RF signal strength. If there is a sudden change in RF signal strength, such as a dropout, or noting that the signal is continuing to weaken, the system performing the reconfiguring may recognize that a transmitter a receiver are moving farther apart. This may provide an indication that signal loss will soon occur, and a switch may be performed proactively to prevent loss of data.

Another example of a proxy for data throughput is rate of change of data upload or download speed, which includes monitoring of changes in a rate of data upload or download between a transmitter and a receiver. In this scenario, while absolute data transmission may still be above a recommended threshold for data transmission, a data upload or download speed that is continuing to deteriorate may indicate that signal loss will soon occur. This may indicate to the system performing the reconfiguring that a changeover in a data pipeline may be performed proactively to prevent loss of data.

Another example of a proxy for data throughput is a signal quality metric that monitors an integrity and performance of a physical layer of a signal, such as bit error rates, modulation error ratios, etc. The signal metric can then be used as a proxy for determining the integrity of the signal, a likelihood that the signal will need to be re-sent, or other impacts to signal quality.

As mentioned above, an actively used data pipeline may be dynamically adapted to maintain continuity of data. Such maintenance may include handling a detour of an actively used data pipeline while the data pipeline map is being changed by a surgical hub or other system.

In one embodiment, a data pipeline being dynamically adapted to maintain continuity of data may include creating a duplicate data stream on a new data pipeline configuration while the new data pipeline connection is stabilizing. For example, a WIFI connection may drop and a cellular (e.g., 5G or other cellular protocol) may pick up after a certain reduction in signal strength.

In creating a duplicate data stream, mission critical portions of the data stream may be directed into an isolated data pipeline from the portions being scaled or adapted. The isolated data pipeline may be reduced in resolution, overlays, or other additions/subtractions to create a minimal data stream that is used while the primary data stream is adapted.

In creating a duplicate data stream, data pipelines/resources may be freed up for use by the new reconfigured pipeline. Other data streams may be reduced in resolution, frequency, or exchange or other aspects that would reduce their resource cost to the data pipelines allowing the system performing the reconfiguring to free up the data pipelines to be reassigned to the newly prioritized adaptive feed. If the freed up data pipelines are not large enough, a plurality of other data pipelines may be reduced or combined to free up multiple new capacity pipelines that can be shared in order to provide the new pipeline volume to moves in-sync.

In one embodiment, a data pipeline being dynamically adapted to maintain continuity of data may include non-seamlessly having data continuity at an appropriate data throughput rate by identifying a trigger event to switch data pipelines. The trigger event may be, for example, pausing data transferring to allow for data pipeline re-configuration to commence. For another example, the trigger event may be buffering data until idle time is available is another option. For yet another example, the trigger event may be non-deterministic single-point data (only latest data matters) with missed datasets being considered as not important.

In one embodiment, a data pipeline being dynamically adapted to maintain continuity of data may include preventing re-occurrence. Preventing re-occurrence may include determining a reason of the need to adjust data pipeline architecture to drive additional system changes that are meant not just to rescale or re-align the data pipeline structure but prevent future similar occurrence for the adaptation if possible. While bandwidth (assuming volume refers to volume of data) may be impacted, the underlying root cause could be different and be resolved in different ways or mechanisms.

One example of a root cause and mechanism for resolving data stream bandwidth issues includes interference. A potential risk is that a communication method may be physically operating on a channel that is subject to interference. This may be due to other services operating on the same wireless spectrum (e.g., multiple Wi-fi modules transmitting simultaneously) or other electromagnetic noise. Such potential risk may be mitigated, for example, by changing the communication method to a different physical service layer (for example, switching 2.4 GHz to 5.0 GHz), which may reduce conflicts, or by utilization of frequency hopping.

Another example of a root cause and mechanism for resolving data stream bandwidth issues includes distance. A potential risk is that a distance between a transmitter and a receiver has become too far. This causes some messages to drop out, requiring the system to retry sending those messages. This results in an effective reduction in the bandwidth of the system and increases the congestion. Such potential risk may be mitigated, for example, by switching the system to a duplicate data stream with a higher output power capacity. This higher power may not be the most efficient, such as in a battery life constrained system. Such potential risk may be mitigated, for another example, by switching the system to a duplicate data stream with a different carrier frequency. The change in frequency may impact its ability to transmit around physical barriers (higher frequency) or greater distance (lower frequency).

Another example of a root cause and mechanism for resolving data stream bandwidth issues includes back-end congestion. A potential risk is that data transfer within a wireless or wired communication methodology may be limited by the back end processing of the system. For example, a wireless system may be able to transmit 1 GBps but the processors within the system may only be able to handle 0.5 GBps of data due to other requests. Such potential risk may be mitigated, for example, by the system allocating more processing to incoming messages, such that they can be received, or finding alternative ways to offload the data processing. Alternatively, the system may be simply constrained by back-end processing rather than the data pipeline itself.

Another example of a root cause and mechanism for resolving data stream bandwidth issues includes overall congestion. A potential risk is that, as congestion increases on a network, more and more devices are negotiating for when to send a message. If enough devices are trying to negotiate, actual message transmission may reduce due to overhead of negotiating messages. Such potential risk may be mitigated, for example, by devices on a network increasing their payload size to reduce the actual number of messages being sent and negotiated. While this may have other impacts on a network's performance, it may allow the network to remain active during this time.

Data pipelines may have multiple layers within a data pipeline. Bandwidth limitations within one aspect may not necessarily limit the whole data pipeline. For example, switching from a wireless 5 Ghz signal to a 2.4 GHz signal will reduce bandwidth but increase range. This represents one portion of the data pipeline, but there may be back-end data limitations.

The data pipeline architecture and configuration may include a fixed data pipeline that has a pre-existing purpose, transformation, data rate, and/or data destination that cannot be altered by the primary system (e.g., the system perform the reconfiguration). The primary system may set up a secondary or backup communication pathway (for example, cellular communication as a backup to Wi-fi communication or, for another example, wired communication as a backup to wireless communication). Data to be sent over a local network is offloaded to the secondary or backup communication pathway.

For example, during a performance of a surgical procedure, a base minimum image of a surgical site that a surgeon (and/or other HCP) sees on a screen of a HID or other display (without any augmentation) is required at all costs to maintain their ability to see the surgical site. A part of any imaging system (and especially an advanced imaging system) may be a parallel pipe to any calculated or augmented pipe that merely utilizes an FPGA to convert the CMOS image voltages into a real-time 60 Hz image. This parallel pipe would be a fixed pipe as it would never be allowed to be re-tasked or adjusted to ensure in a worst case scenario the surgeon (and/or other HCP) always has at least minimal visualization of the surgical site, e.g., always has the base minimum image.

The data pipeline architecture and configuration may include network restrictions. The network restrictions may include data bandwidth, maximum number of devices, quiet time (e.g., 6 pm to 6 am, etc.), and/or localized vs. external facing network restrictions (e.g., all external communication being cutoff during active surgery hours to minimize chances of a cybersecurity attack and, after surgery is completed for the day, communication may be restored to assist in system and software upgrades, etc.).

The data pipeline architecture and configuration may include a common application programming interface (API). The common API may include open API, proprietary API, and/or partner API.

Figure 8:
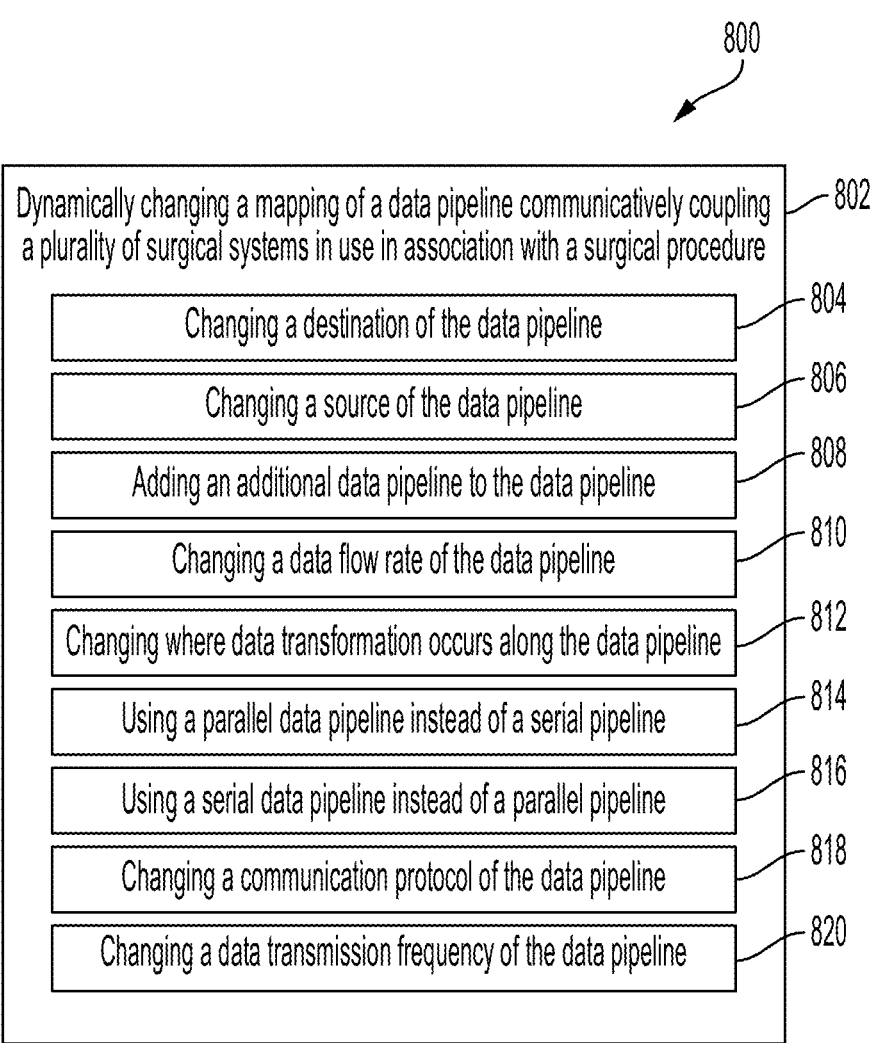
FIG. 8 is a flowchart of one embodiment of a method of changing a data pipeline mapping.

As mentioned above, adjusting data pipeline mapping may include dynamically changing the data pipeline mapping during a performance of a surgical procedure on a patient. FIG. 8 illustrates one embodiment of a method 800 of dynamically changing a data pipeline mapping during a performance of a surgical procedure on a patient. The method 800 may include, in response to a trigger event occurring during a performance of a surgical procedure on a patient, and in real time with the performance of the surgical procedure on the patient, dynamically changing 802, e.g., using a processor of a surgical hub, a cloud-based server, or other system, a mapping of a data pipeline communicatively coupling a plurality of surgical systems in use in association with the surgical procedure. Each of the plurality of surgical systems may be configured to communicate data using the data pipeline. The data may be collected in relation to and in real time with the performance of the surgical procedure and may include at least one of patient data, surgical procedure data, and surgical instrument data. The dynamic changing 802 may include at least one of: changing 804 a destination of the data pipeline, changing 806 a source of the data pipeline, adding 808 an additional data pipeline to the data pipeline, changing 810 a data flow rate of the data pipeline, changing 812 where data transformation occurs along the data pipeline, using 814 a parallel data pipeline instead of a serial pipeline, using 816 a serial data pipeline instead of a parallel pipeline, changing 818 a communication protocol of the data pipeline, and changing 820 a data transmission frequency of the data pipeline.

Computer Systems

A computer system may be suitable for use in implementing computerized components described herein. In broad overview of an exemplary embodiment, the computer system may include a processor configured to perform actions in accordance with instructions, and memory devices configured to store instructions and data. The processor may be in communication, via a bus, with the memory (and/or incorporates the memory) and with at least one network interface controller with a network interface for connecting to external devices, e.g., a computer system (such as a mobile phone, a tablet, a laptop, a server, etc.). The processor may also be configured to be in communication, via the bus, with any other processor(s) of the computer system and with any I/O devices at an I/O interfaces. Generally, a processor will execute instructions received from the memory. In some embodiments, the computer system can be configured within a cloud computing environment, a virtual or containerized computing environment, and/or a web-based microservices environment.

In more detail, the processor can be any logic circuitry that processes instructions, e.g., instructions fetched from the memory. In many embodiments, the processor may be an embedded processor, a microprocessor unit (MPU), microcontroller unit (MCU), field-programmable gate array (FPGA or FGPA), or special purpose processor. The computer system can be based on any processor, e.g., suitable digital signal processor (DSP), or set of processors, capable of operating as described herein. In some embodiments, the processor can be a single core or multi-core processor. In some embodiments, the processor can be composed of multiple processors.

The memory can be any device suitable for storing computer readable data. The memory can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. A computer system can have any number of memory devices.

The memory also can include a cache memory, which is generally a form of high-speed computer memory placed in close proximity to the processor for fast read/write times. In some embodiments, the cache memory is part of, or on the same chip as, the processor.

The network interface controller may be configured to manage data exchanges via the network interface. The network interface controller may handle the physical, media access control, and data link layers of the Open Systems Interconnect (OSI) model for network communication. In some embodiments, some of the network interface controller's tasks may be handled by the processor. In some embodiments, the network interface controller may be part of the processor. In some embodiments, a computer system may have multiple network interface controllers. In some implementations, the network interface may be a connection point for a physical network link, e.g., an RJ 45 connector. In some embodiments, the network interface controller may support wireless network connections and an interface port may be a wireless Bluetooth transceiver. Generally, a computer system can be configured to exchange data with other network devices via physical or wireless links to a network interface. In some embodiments, the network interface controller may implement a network protocol such as LTE, TCP/IP Ethernet, IEEE 802.11, IEEE 802.16, Bluetooth, or the like.

In some uses, the I/O interface may support an input device and/or an output device. In some uses, the input device and the output device may be integrated into the same hardware, e.g., as in a touch screen. In some uses, such as in a server context, there may be no I/O interface or the I/O interface may not be used. In some uses, additional other components may be in communication with the computer system, e.g., external devices connected via a universal serial bus (USB). In some embodiments, an I/O device may be incorporated into the computer system, e.g., a touch screen on a tablet device.

In some implementations, a computer device may include an additional device such as a co-processor, e.g., a math co-processor configured to assist the processor with high precision or complex calculations.

CONCLUSION

Certain illustrative implementations have been described to provide an overall understanding of the principles of the structure, function, manufacture, and use of the systems, devices, and methods disclosed herein. One or more examples of these implementations have been illustrated in the accompanying drawings. Those skilled in the art will understand that the systems, devices, and methods specifically described herein and illustrated in the accompanying drawings are non-limiting illustrative implementations and that the scope of the present invention is defined solely by the claims. The features illustrated or described in connection with one illustrative implementation may be combined with the features of other implementations. Such modifications and variations are intended to be included within the scope of the present invention. Further, in the present disclosure, like-named components of the implementations generally have similar features, and thus within a particular implementation each feature of each like-named component is not necessarily fully elaborated upon.

Approximating language, as used herein throughout the specification and claims, may be applied to modify any quantitative representation that can permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described implementations. Accordingly, the present application is not to be limited by what has been particularly shown and described, except as indicated by the appended claims. All publications and references cited herein are expressly incorporated herein by reference in their entirety for all purposes.

What is claimed is:

1. A surgical data management system, comprising:
a surgical hub comprising:
a processor; and
a memory storing instructions that, when executed by the processor, cause the processor to perform operations comprising:
in response to a trigger event occurring during a performance of a surgical procedure on a patient, and in real time with the performance of the surgical procedure on the patient, dynamically change a mapping of a data pipeline communicatively coupling a plurality of surgical systems in use in association with the surgical procedure;
wherein each of the plurality of surgical systems is configured to communicate data using the data pipeline, the data collected in relation to and in real time with the performance of the surgical procedure and including at least one of patient data, surgical procedure data, and surgical instrument data; and
the dynamic changing comprises at least one of:
changing a destination of the data pipeline,
changing a source of the data pipeline,
adding an additional data pipeline to the data pipeline,
changing a data flow rate of the data pipeline,
changing where data transformation occurs along the data pipeline,
using a parallel data pipeline instead of a serial pipeline,
using a serial data pipeline instead of a parallel pipeline,
changing a communication protocol of the data pipeline, and
changing a data transmission frequency of the data pipeline.

2. The surgical data management system of claim 1, wherein the trigger event is a monitored patient parameter varying outside a predetermined threshold; and
the dynamic changing comprises at least changing where the data transformation occurs along the data pipeline such that untransformed data instead of transformed data is transmitted to at least one of the plurality of surgical systems along the data pipeline.

3. The surgical data management system of claim 1, wherein the trigger event is a monitored patient parameter varying outside a predetermined threshold; and
the dynamic changing comprises at least changing the destination of the data pipeline so the destinations of the data pipeline includes a one of the plurality of surgical systems monitoring the patient parameter.

4. The surgical data management system of claim 3, wherein the instructions, when executed by the processor, further cause the processor to perform operations comprising:
after the dynamic changing, and in response to the monitored patient parameter no longer being outside the predetermined threshold, dynamically changing the mapping again so the so the destination of the data pipeline no longer all includes the one of the plurality of surgical systems monitoring the patient parameter.

5. The surgical data management system of claim 1, wherein the trigger event is a predetermined aspect of the surgical procedure being performed; and
the dynamic changing comprises at least changing where the data transformation occurs along the data pipeline such that untransformed data instead of transformed data is transmitted to at least one of the plurality of surgical systems along the data pipeline.

6. The surgical data management system of claim 1, wherein the trigger event is an additional surgical system connecting to the plurality of data pipelines; and
the dynamic changing comprises at least changing a destination of the data pipeline and changing a source of the data pipeline.

7. The surgical data management system of claim 1, wherein the trigger event is a change in power status of at least one the plurality of surgical systems; and
the dynamic changing comprises at least one of changing a destination of at least one of the plurality of data pipelines, changing the a source of the data pipeline, and changing where the data transformation occurs along the data pipeline.

8. The surgical data management system of claim 1, wherein the trigger event is a change in system status of at least one the plurality of surgical systems; and
the dynamic changing comprises at least changing a destination of the data pipeline.

9. The surgical data management system of claim 1, wherein the trigger event is a change in thermal status of at least one the plurality of surgical systems.

10. The surgical data management system of claim 1, wherein the trigger event is a change in data integrity level of data communicated along at least one the plurality of surgical systems.

11. The surgical data management system of claim 1, wherein the dynamic changing comprises determining a magnitude of change needed for the mapping to reflect a changing need of the data communicated using the data pipeline.

12. The surgical data management system of claim 1, wherein the instructions, when executed by the processor, further cause the processor to perform operations comprising:
when the dynamic changing comprises adding an additional data pipeline to the data pipeline, managing transmission of data on the additional data pipeline to maintain continuity of data.

13. The surgical data management system of claim 1, wherein each of the plurality of surgical systems is one of a hospital network, a database, a surgical instrument, or a surgical cart.

14. A surgical data management system, comprising:
  a cloud-based server comprising:
    a processor; and
    a memory storing instructions that, when executed by the processor, cause the processor to perform operations comprising:
      in response to a trigger event occurring during a performance of a surgical procedure on a patient, and in real time with the performance of the surgical procedure on the patient, dynamically change a mapping of a data pipeline communicatively coupling a plurality of surgical systems in use in association with the surgical procedure;
  wherein each of the plurality of surgical systems is configured to communicate data using the data pipeline, the data collected in relation to and in real time with the performance of the surgical procedure and including at least one of patient data, surgical procedure data, and surgical instrument data; and
  the dynamic changing comprises at least one of:
    changing a destination of the data pipeline,
    changing a source of the data pipeline,
    adding an additional data pipeline to the data pipeline,
    changing a data flow rate of the data pipeline,
    changing where data transformation occurs along the data pipeline,
    using a parallel data pipeline instead of a serial pipeline,
    using a serial data pipeline instead of a parallel pipeline,
    changing a communication protocol of the data pipeline, and
    changing a data transmission frequency of the data pipeline.

15. The surgical data management system of claim 14, wherein each of the plurality of surgical systems is one of a hospital network, a database, a surgical instrument, or a surgical cart.

16. A computer-implemented method, comprising:
  in response to a trigger event occurring during a performance of a surgical procedure on a patient, and in real time with the performance of the surgical procedure on the patient, dynamically change a mapping of a data pipeline communicatively coupling a plurality of surgical systems in use in association with the surgical procedure;
  wherein each of the plurality of surgical systems is configured to communicate data using the data pipeline, the data collected in relation to and in real time with the performance of the surgical procedure and including at least one of patient data, surgical procedure data, and surgical instrument data; and
  the dynamic changing comprises at least one of:
    changing a destination of the data pipeline,
    changing a source of the data pipeline,
    adding an additional data pipeline to the data pipeline,
    changing a data flow rate of the data pipeline,
    changing where data transformation occurs along the data pipeline,
    using a parallel data pipeline instead of a serial pipeline,
    using a serial data pipeline instead of a parallel pipeline,
    changing a communication protocol of the data pipeline, and
    changing a data transmission frequency of the data pipeline.

17. The computer-implemented method of claim 16, wherein each of the plurality of surgical systems is one of a hospital network, a database, a surgical instrument, or a surgical cart.

* * * * *